US011510377B2

(12) United States Patent
Rairdan et al.

(10) Patent No.: US 11,510,377 B2
(45) Date of Patent: *Nov. 29, 2022

(54) POLYNUCLEOTIDES AND METHODS FOR TRANSFERRING RESISTANCE TO ASIAN SOYBEAN RUST

(71) Applicants: Two Blades Foundation, Evanston, IL (US); E. I. Du Pont De Nemours and Company, Wilmington, DE (US); Universidade Federal De Vicosa, Vicosa (BR)

(72) Inventors: Greg Rairdan, Wilmington, DE (US); Karen Broglie, Landenberg, PA (US); Gilda Rauscher, Johnston, IA (US); Hendrikus Pieter van Esse, Norwich (GB); Jonathan D. G. Jones, Norwich (GB); Cintia Goulart Kawashima, Norfolk (GB); Sergio Herminio Brommonschenkel, Vicosa (BR)

(73) Assignees: Two Blades Foundation, Evanston, IL (US); E. I. Du Pont De Nemours aand Company, Wilmington, DE (US); Universidade Federal De Vicosa, Vicosa (BR)

( * ) Notice: Subject to any disclaimer, the term of this patent is extended or adjusted under 35 U.S.C. 154(b) by 2 days.

This patent is subject to a terminal disclaimer.

(21) Appl. No.: 17/081,582

(22) Filed: Oct. 27, 2020

(65) Prior Publication Data

US 2021/0051869 A1 Feb. 25, 2021

Related U.S. Application Data

(63) Continuation of application No. 15/573,149, filed as application No. PCT/US2016/031734 on May 11, 2016, now Pat. No. 10,842,097.

(60) Provisional application No. 62/159,718, filed on May 11, 2015.

(51) Int. Cl.
| | | |
|---|---|---|
| *A01H 1/04* | (2006.01) | |
| *C12N 15/82* | (2006.01) | |
| *C07K 14/415* | (2006.01) | |
| *A01H 1/02* | (2006.01) | |
| *A01N 25/00* | (2006.01) | |
| *A01N 65/20* | (2009.01) | |

(52) U.S. Cl.
CPC ............... *A01H 1/04* (2013.01); *A01H 1/02* (2013.01); *A01N 25/00* (2013.01); *A01N 65/20* (2013.01); *C07K 14/415* (2013.01); *C12N 15/8282* (2013.01)

(58) Field of Classification Search
CPC .................................................. C12N 15/8282
See application file for complete search history.

(56) References Cited

U.S. PATENT DOCUMENTS

| 8,222,486 | B2 | 7/2012 | Douchkov et al. | |
|---|---|---|---|---|
| 10,842,097 | B2 | 11/2020 | Rairdan et al. | |
| 2014/0047579 | A1* | 2/2014 | Schultheiss | .......... C12Y 207/11 |
| | | | | 435/468 |
| 2015/0307890 | A1 | 10/2015 | Wu et al. | |
| 2016/0272987 | A1 | 9/2016 | Gil et al. | |
| 2018/0103600 | A1 | 4/2018 | Rairdan et al. | |

FOREIGN PATENT DOCUMENTS

| AR | P160101358 | 5/2016 |
|---|---|---|
| BR | 112017024429.2 | 5/2016 |
| CA | 2983635 | 5/2016 |
| CN | 201680026961.7 | 5/2016 |
| WO | 2009079729 | 7/2009 |
| WO | 2014117990 | 8/2014 |
| WO | PCT/US2016/031734 | 5/2016 |
| WO | 2016183130 | 11/2016 |

OTHER PUBLICATIONS

Andolfo et al., "Defining the full tomato NB-LRR resistance gene repertoire using genomic and cDNA RenSeq", BMC Plant Biology, 2014, 14:120.
Banerjee et al. (2001) "The leucine-rich repeat domain can determine effective interaction between RPS2 and other host factors in *Arabidopsis* RPS2-mediated disease resistance" Genetics 158:439-450.
Bravo-Almonacid et al., "Field testing, gene flow assessment and pre-commercial studies on transgenic *Solanum tuberosum* spp. *tuberosum* (cv. Spunta) selected for PVY resistance in Argentina", Transgenic Res (2011), 21 (5):967-82.
Brunner S, et al., (2012) "Transgenic Pm3 multilines of wheat show increased powdery mildew resistance in the field", Plant Biotechnology Journal, 10: 398-409.
Burke et al., "Fitness Effects of Transgenic Disease Resistance in Sunflowers", Science (2003), 300(5623):1250.
Cardoso et al., "Transgenic Sweet Orange (*Citrus sinensis* L. Osbeck) Expressing the attacin A Gene for Resistance to *Xanthomonas citri* subsp. *citri*", Plant Mol Biol Rep (2010) 28:185-192.
Cavatorta et al., "Engineering virus resistance using a modified potato gene", Plant Biotechnology Journal (2011), 9, pp. 1014-1021.
Chauhan et al., "The wheat resistance gene Lr34 results in the constitutive induction of multiple defense pathways in transgenic barley", The Plant Journal (2015) 84, 202-215.

(Continued)

*Primary Examiner* — Weihua Fan
(74) *Attorney, Agent, or Firm* — Ballard Spahr LLP

(57) ABSTRACT

Disclosed herein are compostions and methods for improving or enhancing pathogen resistance in legume plants. Compositions comprising polypeptides encoded by legume-derived nucleotide-binding site-leucine-rich repeat (NB-LRR) genes are useful in improving resistance in legumes to Asian soybean rust. Methods of using NB-LRR genes can be used to make a transgenic resistant legume plant.

12 Claims, 3 Drawing Sheets

Specification includes a Sequence Listing.

(56) References Cited

OTHER PUBLICATIONS

Chen et al., "Genetic analysis and molecular mapping of resistance gene to *Phakopsora pachyrhiziin* soybean germplasm SX6907", Theoretical and Applied Genetics, vol. 128, No. 4 (2015), pp. 733-743.
Collinge et al., "Engineering Pathogen Resistance in Crop Plants: Current Trends and Future Prospects", Annu. Rev. Phytopathol. 2010. 48:269-91.
Conrath et al., "Enhanced resistance to Phytophthora infestans and Alternaria solani in leaves and tubers, respectively, of potato plants with decreased activity of the plastidic ATP/ADP transporter", Planta (2003) 19: 75-83.
Dandekar et al., "An engineered innate immune defense protects grapevines from Pierce disease", Proc Natl Acad Sci USA (2012), 109(10):3721-5.
Day, et al., (2005) "Molecular Basis for the RIN4 Negative Regulation of RPS2 Disease Resistance", Plant Cell 17:1292-1305.
Foster S J, et al., (2009) "Rpi-vnt1.1, a Tm-2(2) Homolog From Solanum Venturii, Confers Resistance to Potato Late Blight", Mol Plant Microbe Interact 22: 589-600.
Frost, et al., (2004) "Tobacco Transgenic for the Flax Rust Resistance Gene L Expresses Allele-Specific Activation of Defense Responses", MPMI, 17:224-232.
Fuentes et al., "Intron-hairpin RNA derived from replication associated protein C1 gene confers immunity to Tomato Yellow Leaf Curl Virus infection in transgenic tomato plants", Transgenic Research (2006) 15:291-304.
Gao et al: "Two Classes of Highly Similar Coiled Coil-Nucleotide Binding-Leucine Rich Repeat Genes Isolated from the Rps1-k Locus Encode Phytophthora Resistance in Soybean", Molecular Plant-Microbe Interactions, vol. 18, No. 10, (2005), pp. 1035-1045.
Gomez et al.," FLS2: An LRR Receptor-like Kinase Involved in the Perception of the Bacterial Elicitor Flagellin in *Arabidopsis*", Molecular Cell, vol. 5, 1003-1011, Jun. 2000.
Green et al., "Transgenic Potatoes for Potato Cyst Nematode Control Can Replace Pesticide Use without Impact on Soil Quality", PLoS One (2012) 7(2):e30973.
Gust et al., "Biotechnological concepts for improving plant innate immunity", Curr Opin Biotechnol (2010), 21(2):204-10.
Halterman D. et al., (2008) "Performance of Transgenic Potato Containing the Late Blight Resistance Gene RB", Plant Disease 92: 339-343.
Hartman, "Sources of resistance to Soybean Rust in Perennial Glycine Species", Plant Disease, vol. 76, No. 4, (1992), pp. 396-399.
Hoefle et al., "Transgenic Suppression of Cell Death Limits Penetration Success of the Soybean Rust Fungus *Phakopsora pachyrhizi* into Epidermal Cells of Barley", Phytopathology, (2009) 99(3):220-6.
Horvath D M, et al., (2012) "Transgenic Resistance Confers Effective Field Level Control of Bacterial Spot Disease in Tomato", PLoSONE 7: e42036.
Jan et al., "Expression of a Synthesized Gene Encoding Cationic Peptide Cecropin B in Transgenic Tomato Plants Protects against Bacterial Diseases", Applied and Environmental Microbiology, Feb. 2010, p. 769-775.
Jupe et al., "Resistance gene enrichment sequencing (RenSeq) enables reannotation of the NB-LRR gene family from sequenced plant genomes and rapid mapping of resistance loci in segregating populations", The Plant Journal (2013) 76, 530-544.
Kang et al: "Genome-wide mapping of NBS-LRR genes and their association with disease resistance in soybean", BMC Plant Biology, vol. 12, No. 1, (2012), p. 139.
Kawashima et al: "A pigeon pea gene confers resistance to Asian soybean rust in soybean", Nature Biotechnology, vol. 34, No. 6, (2016), pp. 661-665.
Krens et al., "Performance and long-term stability of the barley hordothionin gene in multiple transgenic apple lines", Transgenic Res (2011) 20:1113-1123.
Lacombe et al., "Interfamily transfer of a plant pattern-recognition receptor confers broad-spectrum bacterial resistance", Nat Biotechnol, (2010),28(4):365-9.
Langenbach et al., "Fighting Asian Soybean Rust", Frontiers in Plant Science, vol. 7, No. 797, Jun. 7, 2016 (2016), pp. 1-13.
Lin et al., "Transgenic tomato plants expressing the *Arabidopsis* NPR1 gene display enhanced resistance to a spectrum of fungal and bacterial diseases", Transgenic Research, 13: 567-581, 2004.
Liu et al., "Transgenic Potato Plants Expressing StoVe1 Exhibit Enhanced Resistance to Verticillium dahliae",Plant Mol Biol Rep (2012) 30:1032-1039.
Lopez-Ochoa et al., "Peptide Aptamers that Bind to a Geminivirus Replication Protein Interfere with Viral Replication in Plant Cells", Journal of Virology, Jun. 2006, p. 5841-5853.
Lorang et al., "Plant disease susceptibility conferred by a "resistance" gene", Proc Natl Acad Sci USA (2007), 104 (37):14861-6.
Mendes et al.," Reduction in susceptibility to Xanthomonas axonopodis pv. citri in transgenic Citrus sinensis expressing the rice Xa21 gene", Plant Pathology (2010) 59, 68-75.
Meyer Jenelle D F et al: "Identification and Analyses of Candidate Genes for Rpp4-Mediated Resistance to Asian Soybean Rust in Soybean", Plant Physiology, American Society of Plant Physiologists, Rockville, MD, US, vol. 150, No. 1, (2009),pp. 295-307.
Moose et al., "Molecular Plant Breeding as the Foundation for 21st Century Crop Improvement",Plant Physiology, Jul. 2008, vol. 147, pp. 969-977.
Namukwaya et al., "Transgenic banana expressing Pflp gene confers enhanced resistance to Xanthomonas wilt disease", Transgenic Res (2011), 21(4):855-65.
Nekrasov et al., "Control of the pattern-recognition receptor EFR by an ER protein complex in plant immunity", The EMBO Journal (2009) 28, 3428-3438.
Park et al., "Molecular breeding for resistance to Phytophthora infestans (Mont.) de Bary in potato (*Solanum tuberosum* L.): a perspective of cisgenesis", Plant Breeding 128, 109-117 (2009).
Ren, et al., (1997) "Genetic suppression of the cereal rye-derived gene Pm8 in wheat", Euphytica, 93:353-360.
Sasu et al., "Indirect costs of a nontarget pathogen mitigate the direct benefits of a virus-resistant transgene in wild Cucurbita", PNAS (2009), 106 (45) 19067-19071.
Seo et al., "A viral resistance gene from common bean functions across plant families and is up-regulated in a non-virus-specific manner", PNAS (2006), vol. 103, No. 32 pp. 11856-11861.
Tai, et al.(1999) "Expression of the Bs2 pepper gene confers resistance to bacterial spot disease in tomato", PNAS, 96: 14153-14158.
Tian, et al. (2003), "Fitness Costs of R-gene-mediated Resistance in *Arabidopsis thaliana*", Nature 423:74-77.
Tricoli et al., "Field Evaluation of Transgenic Squash Containing Single or Multiple Virus Coat Protein Gene Constructs for Resistance to Cucumber Mosaic Virus, Watermelon Mosaic Virus 2, and Zucchini Yellow Mosaic Virus", Bio/Technology, vol. 13, pp. 1458-1465 (1995).
Tripathi et al., "Strategies for resistance to bacterial wilt disease of bananas through genetic engineering", African Journal of Biotechnology, vol. 3 (12), pp. 688-692, (2004).
Tripathi, et al., "Expression of sweet pepper Hrap gene in banana enhances resistance to Xanthomonas campestris pv. musacearum ", Molecular Plant Pathology (2010), 11(6), 721-731.
Truve et al., "Transgenic Potato Plants Expressing Mammalian 2'-5' Oligoadenylate Synthetase are Protected From Potato Virus X Infection Under Field Conditions", Biotechnology (N Y) (1993), 11(9):1048-52.
U.S. Appl. No. 62/159,718, filed May 11, 2015, Greg Rairdan.
U.S. Appl. No. 15/573,149, filed Nov. 10, 2017, Greg Rairdan.
Van esse et al., "Genetic modification to improve disease resistance in crops", New Phytol (2020), 225(1):70-86.
Vanblaere et al.," Molecular characterization of cisgenic lines of apple 'Gala' carrying the Rvi6 scab resistance gene", Plant Biotechnology Journal (2013), pp. 1-8.

(56) References Cited

OTHER PUBLICATIONS

Vishnevetsky et al., "Improved tolerance toward fungal diseases in transgenic Cavendish banana (*Musa* spp. AAA group) cv. Grand Nain", Transgenic Res (2011)20:61-72.
Wang, et al., "Co-transfer and expression of chitinase, glucanase, and bar genes in creeping bentgrass for conferring fungal disease resistance", Plant Science 165 (2003) 497-506.
Yang et al. "Alfafa benefits from Medicago truncatula: the RCT1 gene from M. truncatula confers broad-spectrum resistance to anthracnose in alfafa." Proceedings of the National Academy of Sciences, (2008) 105 (34): 12164-12169.
Zhao et al., "A maize resistance gene functions against bacterial streak disease in rice", PNAS 2005;102;15383-15388.
Zipfel et al., "Perception of the Bacterial PAMP EF-Tu by the Receptor EFR Restricts Agrobacterium-Mediated Transformation", Cell 125, 749-760,(2006).
Zipfel et al., "Bacterial disease resistance in *Arabidopsis* through flagellin perception", Nature (2004), 428 (6984):764-7.
International Search Report and Written Opinion dated Jul. 29, 2016 by the International Searching Authority for International Application No. PCT/US2016/031734, filed on May 11, 2016 and published as WO 2016/183130 dated Nov. 17, 2016 (Applicant—Two Blades Foundation) (14 Pages).
Preliminary Amendment filed on Nov. 10, 2017 with the USPTO for U.S. Appl. No. 15/573,149, filed Nov. 10, 2017, Applicant—Two Blades Foundation); (13 pages).
International Preliminary Report on Patentability dated Nov. 14, 2017 by the International Searching Authority for International Application No. PCT/US2016/031734, filed on May 11, 2016 and published as WO 2016/183130 on Nov. 17, 2016 (Applicant—TWO Blades Foundation) (9 Pages).
Non Final Office dated Sep. 3, 2019 by the USPTO for U.S. Appl. No. 15/573,149, filed Nov. 10, 2017 Applicant—Two Blades Foundation); (16 page).
Response to Non Final Office Action filed on Dec. 3, 2019 with the USPTO for U.S. Appl. No. 15/573,149, filed Nov. 10, 2017, Applicant—Two Blades Foundation); (19 pages).
Notice of Allowance and Fees Due dated Jul. 28, 2020 by the USPTO for U.S. Appl. No. 15/573,149, filed Nov. 10, 2017, Applicant—Two Blades Foundation); (7 pages).
First Office Action dated Sep. 17, 2020 by the State Intellectual Property Office of the People's Republic of China for Chinese Patent Application No. 201680026961.7, which was filed on May 11, 2016 Applicant—Two Blades Foundation); (Translation 15 pages).

\* cited by examiner

POLYNUCLEOTIDES AND METHODS FOR TRANSFERRING RESISTANCE TO ASIAN SOYBEAN RUST

CROSS REFERENCE TO RELATED PATENT APPLICATIONS

This application is a continuation of U.S. application Ser. No. 15/573,149, filed on Nov. 10, 2017, which claims the benefit of priority under 35 U.S.C. 371 of International Application No. PCT/US2016/031734, filed on May 11, 2016, which claims priority to U.S. Provisional Application No. 62/159,718, filed on May 11, 2015 The content of these earlier filed applications is hereby incorporated by reference.

INCORPORATION OF THE SEQUENCE LISTING

The present application contains a sequence listing that was submitted herewith in ASCII format via EFS-Web, containing the file name 36446_0235U3_SL which is 47,733 bytes in size, created on Oct. 26, 2020, and is herein incorporated by reference in its entirety pursuant to 37 C.F.R. § 1.52(e)(5).

FIELD

The present disclosure relates to compositions and methods useful in enhancing pathogen resistance in legume plants, and more particularly in soybean plants, by providing to the plants a gene or gene(s) that are associated with resistance to the causal agent of Asian soybean rust (ASR). The disclosure further relates to polynucleotides capable of enhancing resistance in legumes to ASR and methods of using these polynucleotide sequences to make a transgenic legume plant that is resistant to ASR.

BACKGROUND

Soybeans (*Glycine max*), a major industrial use crop, are also one of the most important protein source crops, and are considered a key food group for preventing disease and optimizing health by many public health organizations including the American Diabetes Association, the American Heart Association and the American Cancer Society. Asian soybean rust (ASR) is a major crop disease affecting soybeans and can negatively affect growth and yield. It is caused by the obligate biotrophic fungus *Phakopsora pachyrhizi* and to a lesser extent, the closely related fungus *Phakopsora meibomiae*. The disease can cause yield losses ranging from 10-90%.

SUMMARY

The present disclosure relates to compositions and methods for identifying rust resistance genes from legume species and transforming those genes into legume crops or a legume crop species, such as *Glycine max*, to generate plants that are resistant to ASR.

Disclosed herein are isolated polynucleotides comprising a nucleotide sequence that encodes a legume-derived NB-LRR polypeptide having at least 90% amino acid sequence identity to a legume sequence disclosed herein. In an aspect, a plant transformed with the polynucleotide displays enhanced resistance to Asian soybean rust when compared to a susceptible plant and/or a non-transformed plant. Also disclosed are recombinant DNA constructs comprising the polynucleotides described herein.

Disclosed herein are useful polypeptides which can include, consist of, or be encoded by a polynucleotide or sequence of SEQ ID NO: 1-8, and variants thereof.

Disclosed herein are methods of conferring disease resistance in a legume crop species (e.g., soybean), the method comprising transforming a legume crop species with a heterologous legume-derived NB-LRR gene that confers disease resistance to a legume crop species disease (e.g., ASR).

Disclosed herein is a transgenic legume crop plant stably transformed with a recombinant DNA construct. In an aspect, the recombinant DNA construct comprises polynucleotides disclosed herein that encode one or more legume-derived NB-LRR resistance genes that are capable of conferring resistance to a plant disease, such as ASR. In an aspect, the polynucleotide comprises one or more non-legume-derived NB-LRR resistance genes and/or non-NB-LRR resistance genes that are capable of conferring resistance to a plant disease. The polynucleotides described herein can also comprise any combination of resistance genes. The transgenic legume crop plant can comprise one or more agronomic traits. Obtaining the seeds from such transgenic legume crop plants is also contemplated. Further, the present disclosure also features a transgenic legume crop plant that is stably transformed that comprises the legume-derived NB-LRR poly nucleotide that has at least 90% sequence identity to a sequence described herein.

Disclosed herein are methods of identifying one or more resistance genes conferring resistance to a plant disease (e.g., ASR).

Disclosed herein are methods of producing an ASR resistant plant (e.g., a legume species). In an aspect, the method comprises transforming a plant cell with a legume-derived NB-LRR resistance gene. The method can further comprise regenerating the transformed plant from the transformed plant cell. In an aspect, the method comprises growing the transformed plant such that the expression of the legume-derived NB-LRR resistance gene produces a transformed plant that displays enhanced resistance to ASR disease.

Disclosed herein are methods of producing a legume plant that is a progeny from a cross with a legume plant comprising a legume-derived NB-LRR resistance gene described herein.

Disclosed herein are methods of assaying a legume plant for disease resistance to a plant disease (e.g, ASR). In an aspect, the method comprises exposing a portion of the legume plant to a plant pathogen (e.g., *Phakopsora pachyrhizi*); measuring plant disease symptoms on the legume plant exposed to the plant pathogen; and comparing the plant disease symptoms to a reference standard for disease resistance.

Disclosed herein are methods of enhancing plant resistance to ASR disease. In an aspect, the method comprises conferring resistance to an ASR pathogen (e.g., *Phakopsora pachyrhizi*) by introgression of a legume-derived NB-LRR resistance gene into germplasm (e.g., a legume crop species) in a breeding program for resistance to ASR. The method features a legume-derived NB-LRR resistance gene that encodes an NB-LRR polypeptide. In an aspect, the NB-LRR polypeptide comprises an amino acid sequence having at least 90% homology to a legume-derived NB-LRR polypeptide disclosed herein. The method described herein also features a plant transformed with the polypeptide that displays enhanced resistance to ASR when compared to a susceptible plant.

DETAILED DESCRIPTION

Figure 1:
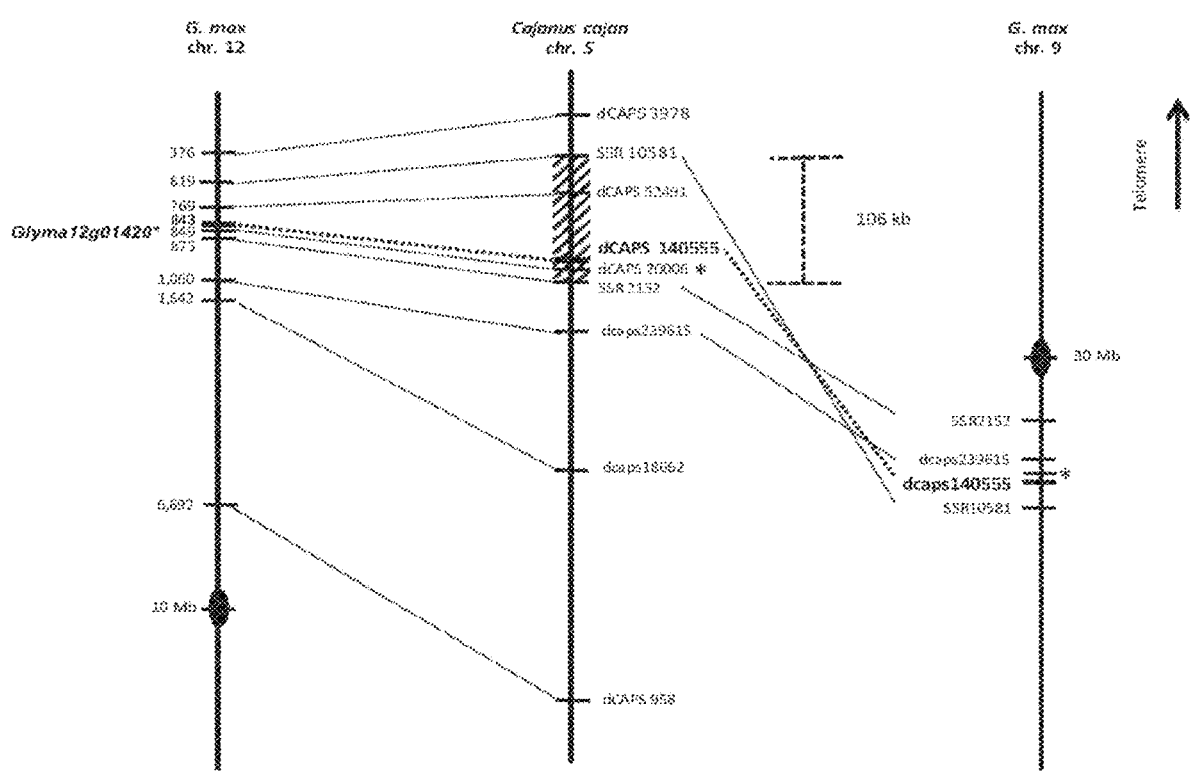
FIG. 1 illustrates that the CcRpp1 genetic region in *Cajanus cajan* was syntenic with genomic regions from *Glycine max* chromosomes 12 and 9. The marker dCAPS140555 tightly linked to CcRpp1 in 0119-99 was positioned close to a single syntenic NB-LRR gene (Glyma12g01420) in *Glycine max* (indicated, "*"). Similarly, the CAPS20006 marker, which is located in a *Cajanus cajan* gene, is positioned in the homologous *Glycine max* gene Glyma12g01420.

Crop diseases cause serious crop management issues and can sometimes lead to total crop failure. Asian soybean rust is a threat to world soybean production and is currently addressed by the use of foliar fungicides. Stable and reliable genetic resistance in commercial plant lines is an important feature associated with soybean crop yields, and presently, commercially grown soybean cultivars that are fully resistant to Asian soybean rust caused by *Phakopsora pachyrhizi*, are not available. The causal agents of ASR. *Phakopsora pachyrhizi* and *Phakopsora meibomiae*, infect leaf tissue from a broad range of leguminous plants (at least 31 species in 17 genera; Slaminko et a. (2008) Plant Dis., 92:797-771; and at least 42 species in 19 genera; Frederick et al. (2002) Mycology, 92.217-227, respectively). In total, a further 152 species in other genera have been described to be potential hosts of *Phakopsora pachyrhizi* (Bonde et al. (2008) Plant Dis., 92:30-38; Goellner et al. (2010) Molecular Plant Pathology, 11:169-177; Ono et al (1992) Mycol. Res., 96(10):825-850; and Slaminko et al. (2008) Plant Dis., 92:797-771). Currently, fungicide applications are the only available method to mitigate ASR.

Presently, no commercially grown soybean (*Glycine max*) cultivars are available that are fully resistant to *Phakopsora pachyrhizi*. Resistance to *Phakopsora pachyrhizi* in soybeans is rare; USDA evaluated the entire USA soybean germplasm collection and found that fewer than 5% were resistant or partially resistant to *Phakopsora pachyrhizi*. Furthermore, the genes available in these soybean accessions only provide resistance that is isolate-specific; therefore these sources are not able to provide durable resistance under field conditions such as where multiple races are present.

Given that ASR is a major threat to soybean production, it is beneficial to identify sources of resistance genes and incorporate these transgenic genes into legume germplasm, such as *Glycine max*, for enhanced protection. To identify novel resistance genes, several non-*Glycine max* legume species were screened for variation in resistance to *Phakopsora pachyrhizi*. Dominant resistance genes in several legumes were identified and confirmed to be members of the well-characterized class of resistance (R) genes, the nucleotide binding domain leucine-rich repeat (NB-LRR) gene family. When transferred to soybeans, for example, either as a single gene, multiple genes, or in a multi-gene cassette, these resistance genes can provide resistance to *Phakopsora pachyrhizi* via heterologous expression.

Although the transfer of resistance genes between plant species has been attempted, in large part, it has been unsuccessful or associated with fitness penalties (Tai et al. (1999) PNAS, 96: 14153-14158; Ren et al. (1997) Euphytica, 93:333-360; Day et al. (2005) Plant Cell 17:1292-1305; Banerjee et al. (2001) Genetics 158:439-450; Tian et al. (2003), Nature 423:74-77; and Frost et al. (2004) MPMI, 17:224-232). And, while the successful transfer of resistance has been achieved in some plants (Halterman D., et a. (2008) Plant Disease 92: 339-343 (potato, Foster S J, et al. (2009) Mol Plant Microbe Interact 22: 589-600 (potato); Brunner S, et al. (2012) Plant Biotechnology Journal 10: 398-409 (wheat); and Horvath D M, et al. (2012) PLoS ONE 7: e42036 (tomato)), resistance to *Phakopsora pachyrhizi* in say beans by R gene transfer has not been previously achieved.

Plants can defend themselves through a variety of cellular mechanisms. It is currently understood that the plant immune system is made up of receptors on the outside (often called the first tier immunity) and the inside of a cell (often referred to as the second tier immunity). Both sets of receptors can detect and respond to a pathogen. The first tier responds to primary elements of a pathogen resulting in activation of pathogen-associated molecular pattern (PAMP)-triggered immunity. Successful pathogens overcome PAMP-triggered immunity by secreting molecules called "effector proteins" or "effectors" that are either localized to the plant apoplast or are taken up into the plant cell. Effectors manipulate host cell functions to suppress host immune responses in order to facilitate the establishment of infection or to otherwise enhance growth conditions for the pathogen, e.g. by ensuring availability to nutrients. Plants have, in some cases, evolved a second tier of immunity in which R gene products recognize the activity of specific effectors resulting in an effector-triggered immunity.

Resistance (R) genes in plant genomes produce R proteins that recognize specific pathogen effectors. The largest class of R genes codes for proteins that contain a nucleotide binding (NB) domain and leucine-rich repeat (LRR) domains, designated "NB-LRR" and guards the intracellular environment. The second class of R genes codes for proteins that consist of an extracellular membrane-anchored LRR domain coupled to a receptor-like domain and is called a receptor-like protein (RLP). The RLP class is often coupled to receptor-like kinases and monitors the exterior of a cell, R proteins convey disease resistance to a pathogen through either direct binding of pathogen effectors or indirect action of a pathogen effector on a host cell target.

As a result of the "arms race" between host and pathogen, pathogen effectors can have either an avirulence or virulence effect. The virulence activity of effectors is associated with the manipulation of normal host cell functions or the suppression of host immune responses by the pathogen in order to establish successful infection. In avirulence, recognition by the corresponding plant R protein activates a host immune or defense response, resulting in programmed cell death and resistance to the pathogen.

Major gene resistance, which relies on a one to one correspondence ("gene-for-gene relationship") between pathogen effectors and plant resistance genes, has been widely used in breeding approaches. Such resistance based on the introduction of a single R gene, however, is typically race-specific and easily overcome by single mutations in the pathogen avr gene as a consequence of diversifying selection to avoid recognition by the host. Thus, the durability of such qualitative resistance is of concern. Attempts have been made to introduce novel antimicrobial/antifungal genes or to modify expression of endogenous defense-related genes in transgenic plants. In many cases, however, the effect is only partial or short-lasting and can come at a cost to plant yield and/or vigor. Thus, an effective use of R genes remains one of the most effective ways to engineer resistance. Furthermore, although individual R genes can be rapidly overcome by a pathogen, successful introgression of several R genes simultaneously can provide durable race-independent resistance to pathogen isolates. For instance, the use of gene stacking, the process of combining two or more genes of interest into a single plant, can be an effective strategy to provide disease resistance. An example of successful gene stacking of R genes is the introgression of the Cf-9 resistance locus into tomato in the 1970's, which effectively halted problems with tomato leaf mold caused by *Cladosporium fulvum*. Using classical breeding to generate an effective "stack" of multiple R genes in crops, however, is often hampered by the dominant nature of R genes, and in crops such as soy, the availability of R genes.

The nucleic acids and polypeptides disclosed herein are useful in methods for conferring or enhancing or increasing fungal resistance to a plant (e.g., a legume crop species). Methods and compositions disclosed herein may comprise the following polypeptide and polynucleotides sequences:

SEQ ID NO: 1 CcRpp1 gene from *Cajanus cajan* (polynucleotide sequence) (NB-LRR-2)

SEQ ID NO: 2: CcRpp1 (polypeptide sequence) (NB-LRR-2)

SEQ ID NO: 3: NB-LRR-1 (polynucleotide sequence)

SEQ ID NO: 4: N-LRR-1 (polypeptide sequence)

SEQ ID NO: 5: NB-LRR-3 (polynucleotide sequence)

SEQ ID NO: 6: NB-LRR-3 (polypeptide sequence)

SEQ ID NO: 7 NB-LRR-4 (polynucleotide sequence)

SEQ TD NO: 8: NB-LRR-4 (polypeptide sequence)

Compositions and methods disclosed herein are useful in protecting plants from fungal pathogens. The interactions between a host and a pathogen can be described in a continuum of "immunity," to "partial resistance" to "susceptibility." The terms "immunity" or "immune" are used herein to mean the absence of any macroscopically visible disease symptom(s). The term "partial resistance" is used herein to mean the presence of macroscopically visible lesions with no or limited sporulation, and/or a reduction in the extent or degree and/or a delay in the progression of any disease symptom(s) and can be, for example, manifested as reduced number of lesions or lesions with a reduction in sporulation. As used herein, the term "susceptibility" or the phrase "lack of resistance" to ASR refers to the occurrence of lesions with sporulation levels equal to or above the sporulation level observed in a reference standard, such as, for example, cultivars Williams or Peking.

The term "resistance" is used herein to mean an absence or reduction of one or more disease symptoms in a plant caused by a plant pathogen. Resistance can mean that disease symptoms, such as, for example, number of lesions, defoliation, and associated yield loss, are reduced, minimized or lessened, when compared to a plant that is susceptible to the disease or a plant that does not contain an effective resistance gene, such as, for example, a NB-LRR gene that reduces one or more disease symptoms. Further, resistance can include the prevention or delay of proliferation of a pathogen (e.g., fungi). In a broad sense, the term "resistance" includes immunity and partial resistance as defined above.

"Plant pathogen" or "fungal pathogen" can be used herein to mean fungal pathogens of, for example, the genus *Phakopsora*, including the species *Phakopsora pachyrhizi* and *Phakopsora meibomiae*. These species are known to cause ASR in plants. A plant disease or a legume crop species disease, for example, can be ASR.

Methods of the present disclosure can be carried out, for example, to provide enhanced resistance by *Glycine max* to the obligate biotrophic fungus *Phakopsora pachyrhizi*, the main causal agent of ASR, or to *Phakopsora meibomiae*. For example, increased or enhanced resistance to a fungal pathogen may be compared to the response of a susceptible plant, such as, for example, Williams or Peking. Resistance an vary and is related to the proportion (i.e., percent) of disease symptoms (e.g., lesions) observed on a plant or plant part (e.g., leaf). A numerical score or value for immunity, resistance and susceptibility can be given. For example, a numerical score for resistance represents the degree of resistance a plant exhibits to a plant disease (e.g., ASR). The numerical scores can also be used to compare the degree of resistance, for example, between a plant of interest (e.g., a transgenic legume crop plant) to that of a susceptible plant (e.g., Williams or Peking) or a reference standard.

Methods and compositions for resistance disclosed herein relate to the isolation of one or more resistance genes from a legume species, and the subsequent transfer of one or more of these resistance genes to another plant, soybeans, for example, to provide resistance to *Phakopsora* spp. via homologous or heterologous expression. The term "disease resistance gene" or "resistance gene" is used herein to mean a gene that encodes a protein or polypeptide capable of enhancing or improving a defense or immune system response in a plant. An aspect of the present disclosure comprises the transfer of a functioning R gene to a sexually compatible or incompatible species to produce disease resistance. Polypeptides and R genes (e.g., NB-LRR polypeptides and NB-LRR genes) described herein can be used alone or in a stack with other R genes or in a stack with non-R genes (including non-NB-LRR resistance genes) to provide resistance to ASR.

The transgenic approach of the present disclosure therefore can be used alone or in combination with other strategies to produce or confer ASR resistance in plants. Other useful strategies include, but are not limited to, blocking the functional activity of effectors, inhibiting the uptake of a pathogen or pathogen factors (e.g., fungi) into the host cell (e.g., plant cell) and/or conventional breeding for resistance.

Methods of the present disclosure can provide or enhance the resistance of a plant, such that the causal agents of a disease, such as ASR, can no longer reproduce. The term "enhance" means to improve, increase, amplify, multiply, elevate and/or raise, thereby reducing one or more disease symptoms. Accordingly, plants (e.g., soybean) exhibit an increased resistance to a disease (e.g., ASR) when compared to plants that are susceptible or tolerant to *Phakopsora* spp. In an aspect, methods described herein can reduce one or more symptoms (i.e., disease symptoms) of a legume plant disease (e.g., ASR). A method can comprise exposing a transgenic legume crop plant (e.g., soybean) to a legume plant disease resulting in the transgenic legume crop plant having enhanced resistance to the plant disease. In some aspects, the transgenic legume crop plant comprises one or more legume-derived NB-LRR polynucleotides. One or more legume-derived NB-LRR polynucleotides may have at least 90% sequence identity to a sequence as disclosed herein.

The term "plant" is used herein to include any plant, tissues or organs (e.g., plant parts). Plant parts include, but are not limited to, cells, stems, roots, flowers, ovules, stamens, seeds, leaves, that can be cultured into a whole plant. A plant cell is a cell of a plant, either taken directly from a seed or plant, or derived through culture from a cell taken from a plant. Progeny, variants, and mutants of the regenerated plants are within the scope of the present disclosure, provided that these parts comprise the introduced polynucleotides.

In an aspect, the plant, plant part, or plant cell is derived from a plant including but not limited to, alfalfa, clover, peas, beans, lentils, lupins, mesquite, carob, soybeans, peanuts, and tamarind.

In an aspect, the plant is a legume. In an aspect, the NB-LRR polypeptide, NB-LRR polynucleotide, and/or NB-LRR resistance gene (or NB-LRR gene) is derived from a legume. Examples of legumes include, but are not limited to, the genus *Phaseolus* (e.g., French bean, dwarf bean, climbing bean (*Phaseolus vulgaris*), Lima bean (*Phaseolus lunatus*), Tepary bean (*Phaseolus acutfolius*), runner bean (*Phaseolus coccineus*)); the genus *Glycine* (e.g., *Glycine soja* soybeans (*Glycine max* (L.))); pea (*Pisum*) (e.g., shelling peas (sometime called smooth or roundseeded peas; *Pisum sativum*); marrowfat pea (*Pisum sativum*), sugar pea (*Pisum sativum*), also called snow pea, edible-podded pea or mangetout, (*Pisum granda*)); peanut (*Arachis hypgaea*), clover (*Trifolium* spp.) medick (*Medicago*), kudzu vine (*Pueraria lobata*) common lucerne, alfalfa (*Medicago sativa*), chickpea (*Cicer*), lentils (*Lens culinaris*), lupins (*Lupinus*); vetches (*Vicia*), field bean, broad bean (*Vicia faba*), vetchling (*Lathyrus*) (e.g., chickling pea (*Lathyrus sativus*), heath pea (*Lathyrus tuberosus*)); genus *Vigna* (e.g., moth bean (*Vigna aconitifolia*), adzuki bean (*Vigna angularis*), urd bean (*Vigna mungo*), mung bean (*Vigna radiata*), bambara groundnut (*Vigna subterrane*), rice bean (*Vigna umbellata*), *Vigna vexillata, Vigna unguiculata* (also known as asparagus bean, cowpea)); pigeon pea (*Cajanus cajan*), the genus *Macrotyloma* (e.g., geocarpa groundnut (*Macrotyloma geocarpum*), horse bean (*Macrotyloma uniflorum*; goa bean (*Psophocarpus tetragonolohus*, African yam bean (*Sphenostylis stenocarpa*). Egyptian black bean, lablab bean (*Lablab purpureus*), yam bean (*Pachyrhizus erosus*), guar bean (*Cyamopsis tetragonolobus*); and/or the genus *Canavalia* (e.g. jack bean (*Canavalia ensiformis*)), sword bean (*Canavalia gladiata*).

Compositions and methods described herein can result in an agronomically desirable line or variety. Agronomic characteristics or traits include, but are not limited to, herbicide tolerance, increased yield, insect control, weed control, pest control, pathogen disease resistance (e.g., fungal, virus, bacterial), high protein production, germination and seedling growth control, enhanced nutrition, environmental stress resistance, increased digestibility, male sterility, flowering time, or transformation technology traits such as cell cycle regulation and/or gene targeting.

The present disclosure provides a method for screening or assaying legume plants for resistance, immunity, or susceptibility to a plant disease. Determination of resistance, immunity, or susceptibility of a plant to a particular pathogen is known to one skilled in the art A method for screening or assaying legume plants for resistance, immunity or susceptibility to a plant disease comprises exposing a plant cell, tissue or organ (e.g., leaf) to a pathogen (e.g., *Phakopsora pachyrhizi*) and then determining and/or measuring in the exposed plant, the degree of resistance, immunity and/or susceptibility to a plant disease (e.g., ASR) caused by the pathogen. The method can further comprise measuring any observable plant disease symptoms on the plant exposed to the plant pathogen and then comparing the plant disease symptoms to a reference standard to determine the degree or extent of disease resistance.

Methods of exposing a plant cell, tissue or organ to a pathogen are known in the art. Methods of measuring, comparing, and determining the level of resistance, immunity and/or susceptibility (e.g., plant disease symptoms) to a disease, such as, for example, ASR, caused by the pathogen are also well known in the art. The exposed plants can be further assessed to isolate polynucleotides, amino acid sequences and/or genetic markers that are associated with, linked to, and/or confer resistance, immunity or susceptibility of a plant to a particular pathogen or disease. Further assessments include, but are not limited to, isolating polynucleotides, nucleic acids, or amino acids sequences from the exposed plant, carrying out an assay of the isolated polynucleotides or nucleic acids, for example, to detect one or more biological or molecular markers associated with one or more agronomic characteristics or traits, including but not limited to, resistance, immunity and/or susceptibility. The information gleaned from such methods can be used, for example, in a breeding program.

In the present disclosure, "nucleic acid" refers to a deoxyribonucleotide or ribonucleotide polymer in either single- or double-stranded form, and unless otherwise limited, encompasses known analogues (e.g., peptide nucleic acids) having the essential nature of natural nucleotides in that they hybridize to single-stranded nucleic acids in a manner similar to naturally occurring nucleotides.

The terms "polypeptide," "peptide," and "protein" are used interchangeably herein to refer to a polymer of amino acid residues. The terms apply to amino acid polymers in which one or more amino acid residues is an artificial chemical analogue of a corresponding naturally occurring amino acid, as well as to naturally occurring amino acid polymers. Polypeptides of the present disclosure can be produced either from a nucleic acid disclosed herein, or by the use of standard molecular biology techniques. For example, a truncated protein of the present disclosure can be produced by expression of a recombinant nucleic acid of the embodiments in an appropriate host cell, or alternatively by a combination of ex vivo procedures, such as protease digestion and purification.

The term "encode" is used herein to mean that the nucleic acid comprises the required information, specified by the use of codons to direct translation of the nucleotide sequence (e.g., a legume sequence) into a specified protein. A nucleic acid encoding a protein can comprise non-translated sequences (e.g., introns) within translated regions of the nucleic acid or can lack such intervening non-translated sequences (e.g., as in cDNA).

Aspects of the disclosure encompass isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material, or culture medium when produced by recombinant techniques (e.g. PCR amplification), or substantially free of chemical precursors or other chemicals when chemically synthesized. Optimally, an "isolated" polynucleotide is free of sequences (for example, protein encoding sequences) that naturally flank the polynucleotide (i.e., sequences located at the 5' and 3' ends of the polynucleotide) in the genomic DNA of the organism from which the polynucleotide is derived. For example, in some embodiments of the disclosure, the isolated polynucleotide can contain less than about 5 kb, about 4 kb, about 3 kb, about 2 kb, about 1 kb, about 0.5 kb, or about 0.1 kb of nucleotide sequence that naturally flank the polynucleotide in genomic DNA of the cell from which the polynucleotide is derived. A protein that is substantially free of cellular material includes preparations of protein having less than about 30%, about 20%, about 10%, about 5%, or about 1% (by dry weight) of contaminating protein. When the protein of the embodiments, or a biologically active portion thereof is recombinantly produced, optimally culture medium represents less than about 30%, about 20%, about 10%, about 5%, or about 1% (by dry weight) of chemical precursors or non-protein-of-interest chemicals.

Fragments and variants relating to the nucleotide sequences and proteins encoded are within the scope of the present disclosure. A "fragment" refers to a portion of the nucleotide sequence or a portion of the amino acid sequence and thus the protein encoded thereby. Fragments of a nucleotide sequence can encode protein fragments that retain the biological activity of the native protein and have the ability to confer resistance (i.e., fungal resistance) upon a plant. Alternatively, fragments of a nucleotide sequence, that are useful as hybridization probes, do not necessarily encode fragment proteins retaining biological activity. Thus, fragments of a nucleotide sequence can range from at least about 15 nucleotides, about 50 nucleotides, about 100 nucleotides, and up to the full-length nucleotide sequence encoding the polypeptides of the present disclosure.

A fragment of a nucleotide sequence that encodes a biologically active portion of a polypeptide of the present disclosure can encode at least about 15, about 25, about 30, about 40, or 45 about 50 contiguous amino acids, or up to the total number of amino acids present in a full-length polypeptide of the embodiments (for example, 923 amino acids for the peptide encoded by SEQ ID NO: 1). Fragments of a nucleotide sequence that are useful as hybridization probes or PCR primers generally need not encode a biologically active portion of a protein.

The term "full-length sequence," when referring to a specified polynucleotide, means having the entire nucleic acid sequence of a native sequence. "Native sequence" is used herein to mean an endogenous sequence, i.e., a non-engineered sequence found in an organism's genome.

Thus, a fragment of a nucleotide sequence of the present disclosure can encode a biologically active portion of a polypeptide, or it can be a fragment that can be used as a hybridization probe or PCR primer using methods disclosed below. A biologically active portion of a polypeptide conferring resistance can be prepared by isolating a portion of one of the nucleotide sequences of the embodiments, expressing the encoded portion of the protein and assessing the ability of the encoded portion of the protein to confer or enhance fungal resistance in a plant. Nucleic acid molecules that are fragments of a nucleotide sequence of the embodiments comprise at least about 15, about 20, about 50, about 75, about 100, or about 150 nucleotides, or up to the number of nucleotides present in a full-length nucleotide sequence disclosed herein (for example, 2,778 nucleotides for SEQ ID NO: 1).

The term "variants" means substantially similar sequences. For polynucleotides, a variant comprises a deletion and/or addition of one or more nucleotides at one or more sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. One of skill in the art can recognize that variants of the nucleic acids of the embodiments will be constructed such that the open reading frame is maintained. For polynucleotides, conservative variants include those sequences that, because of the degeneracy of the genetic code, encode the amino acid sequence of one of the polypeptides of the embodiments. Naturally occurring allelic variants such as these can be identified with the use of well-known molecular biology techniques, as, for example, with polymerase chain reaction (PCR) and hybridization techniques as outline below. Variant polynucleotides also include synthetically derived polynucleotides, such as those generated, for example, by using site-directed mutagenesis but which still encode a protein of the embodiments. Generally, variants of a particular polynucleotide of the present disclosure can have at least about 40%, about 45% about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to that particular polynucleotide as determined by sequence alignment programs well known in the art.

Variants of a particular polynucleotide of the embodiments (i.e., the reference polynucleotide) can also be evaluated by comparison of the percent sequence identity between the polypeptide encoded by a variant polynucleotide and the polypeptide encoded by the reference polynucleotide. Percent sequence identity between any two polypeptides can be calculated using sequence alignment programs known in the art. Where any given pair of polynucleotides of the present disclosure is evaluated by comparison of the percent sequence identity shared by the two polypeptides they encode, wherein the percent sequence identity between the two encoded polypeptides is at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity.

"Variant protein" means a protein derived from the native protein by deletion or addition of one or more amino acids at one or more sites in the native protein and/or substitution of one or more amino acids at one or more sites in the native protein. Variant proteins encompassed by some aspects of the present disclosure are biologically active, that is they continue to possess the desired biological activity of the native protein, which is, the ability to confer or enhance plant resistance (i.e., plant fungal pathogen resistance) as described herein. Such variants can result, for example, from genetic polymorphism or from human manipulation. Biologically active variants of a native protein of the embodiments can have at least about 40%, about 45%, about 50%, about 55%, about 60%, about 65%, about 70%, about 75%, about 80%, about 85%, about 90%, about 91%, about 92%, about 93%, about 94%, about 95%, about 96%, about 97%, about 98%, about 99% or more sequence identity to the amino acid sequence for the native protein as determined by sequence alignment programs known in the art. A biologically active variant of a protein of the present disclosure can differ from that protein by as few as about 1-15 amino acid residues, as few as about 1-10, such as about 6-10, as few as about 5, as few as 4, 3, 2, or even 1 amino acid residue.

The proteins disclosed herein can be altered, for example, by including amino acid substitutions, deletions, truncations, and insertions. Methods for such manipulations are known in the art. For example, amino acid sequence variants and fragments of the resistance proteins can be prepared by mutations in the DNA. Methods for mutagenesis and polynucleotide alterations are known in the art.

Variant polynucleotides and proteins also encompass sequences and proteins derived from mutagenic or recombinogenic procedures, including and not limited to procedures such as DNA shuffling. Libraries of recombinant polynucleotides can be generated from a population of related sequence polynucleotides comprising sequence regions that have substantial sequence identity and can be homologously recombined in vitro or in vivo. For example, using this approach, sequence motifs encoding a domain of interest can be shuffled between the protein gene of the present disclosure and other known protein genes to obtain a new gene coding for a protein with an improved property of interest, such as increased ability to confer or enhance plant resistance to a fungal pathogen Strategies for such DNA shuffling are known in the art.

The polynucleotides described herewith can be used to isolate corresponding sequences from other organisms, particularly other plants. In this manner, methods such as PCR or hybridization can be used to identify such sequences based on their sequence homology to the sequences set forth herein. Sequences isolated based on their sequence identity to the entire sequences set forth herein or to variants and fragments thereof are encompassed by the present disclosure. Such sequences include sequences that are orthologs of the disclosed sequences. The term "orthologs" refers to genes derived from a common ancestral gene and which are found in different species as a result of speciation. Genes found in different species are considered orthologs when their nucleotide sequences and/or their encoded protein sequences share at least about 60%, about 70%, about 75%, about 80%, about 85%, about 90%, about 91%, about 92%, about 93%, about 94%, about 95%, about 96%, about 97%, about 98%, about 99%, or greater sequence identity. Functions of orthologs are often highly conserved among species Tus, isolated polynucleotides that encode for a protein that confers or enhances fungal plant pathogen resistance and that hybridize to the sequences disclosed herein, or to variants or fragments thereof, are encompassed by the present disclosure.

In a PCR approach, oligonucleotide primers can be designed for use in PCR reactions to amplify corresponding DNA sequences from cDNA or genomic DNA extracted from any organism of interest. Methods for designing PCR primers and PCR cloning are known in the art and are disclosed in Sambrook et al. (1989) *Molecular Cloning: A Laboratory Manual* (2d ed., Cold Spring Harbor Laboratory Press. Plainview, N.Y.). Known methods of PCR include, and are not limited to, methods using paired primers, nested primes, single specific primers, degenerate primers, gene-specific primers, vector-specific primers, partially-mismatched primers, and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes can be genomic DNA fragments, cDNA fragments, RNA fragments, or other oligonucleotides, and can be labeled with a detectable group such as $^{32}P$, or any other detectable marker. Thus, for example, probes for hybridization can be made by labeling synthetic oligonucleotides based on the polynucleotides of the embodiments. Methods for preparation of probes for hybridization and for construction of cDNA and genomic libraries are known in the art.

Various procedures can be used to check for the presence or absence of a particular sequence of DNA, RNA, or a protein. These include, for example, Southern blots, northern blots, western blots, and ELISA analysis. These techniques are well known in the art.

The compositions and methods of the present disclosure are useful for modulating the levels of one or more proteins in a plant. The term "modulate" is used herein to mean an increase or decrease in the level of a protein within a genetically altered (i.e., transformed) plant relative to the level of that protein from the corresponding non-transformed plant (i.e., a plant not genetically altered in accordance with the methods of the present disclosure).

The terms "inhibit," "inhibition," "inhibiting", "reduced". "reduction" and the like as used herein to mean any decrease in the expression or function of a target gene product, including any relative decrease in expression or function up to and including complete abrogation of expression or function of the target gene product.

The terms "increase," "increasing," "enhance." "enhancing" and the like are used herein to mean any boost or gain or rise in the expression, function or activity of a target gene (e.g., R gene) product providing an increased resistance to one or more pathogens (e.g., *Phakopsora* spp.) or to a disease (e.g., ASR) compared to a susceptible plant. Further, the terms "induce" or "increase" as used herein can mean higher expression of a target gene product, such that the level is increased 10% or more, 50% or more or 100% relative to a cell or plant lacking the target gene or protein of the present disclosure.

The term "expression" as used herein in refers to the biosynthesis or process by which a polynucleotide, for example, is produced, including the transcription and/or translation of a gene product. For example, a polynucleotide of the present disclosure can be transcribed from a DNA template (such as into an mRNA or other RNA transcript) and/or the process by which a transcribed mRNA is subsequently translated into a polypeptide or protein. The term "gene product" can refer to for example, transcripts and encoded polypeptides. Inhibition of (or increase in) expression or function of a gene product (i.e., a gene product of interest) can be in the context of a comparison between any two plants, for example, expression or function of a gene product in a genetically altered plant versus the expression or function of that gene product in a corresponding, but susceptible wild-type plant or other susceptible plant. The expression level of a gene product in a wild-type plant can be absent. For example, a "wild-type" plant can be a plant, plant cell or plant part that does not express an exogenous NB-LRR nucleic acid or exogenous NB-LRR protein.

Alternatively, inhibition of (or increase m) expression or function of the target gene product can be in the context of a comparison between plant cells, organelles, organs, tissues, or plant parts within the same plant or between plants, and includes comparisons between developmental or temporal stages within the same plant or between plants. Any method or composition that down-regulates expression of a target gene product, either at the level of transcription or translation, or down-regulates functional activity of the target gene product can be used to achieve inhibition of expression or function of the target gene product. Similarly, any method or composition that induces or up-regulates expression of a target gene product, either at the level of transcription or translation, or increases or activates or up-regulates functional activity of the target gene product can be used to achieve increased expression or function of the target gene or protein. Methods for inhibiting or enhancing gene expression are well known in the art.

The genes and polynucleotides of the present disclosure include naturally occurring sequences as well as mutant or altered forms. The proteins disclosed herein also encompass naturally occurring proteins as well as variations, fragments and modified forms thereof. Such variants and fragments will continue to possess the desired ability to confer or enhance plant fungal pathogen resistance. In an aspect, mutations made in the DNA encoding the variant or fragments thereof generally do not place the sequence out of the reading frame and optimally will not create complementary regions that could produce secondary mRNA structure.

The gene or genes of the present disclosure can be expressed as a transgene in order to make plants resistant to ASR. The use of different promoters described herein or known to those of skill in the art will allow the gene's expression to be modulated in different circumstances (i.e., the promoters can be selected based on the desired outcome). For instance, higher levels of expression in a particular tissue system or organ (e.g., leaves) may be desired to enhance resistance. The entire gene can be inserted (e.g., both native promoter and coding sequence), as a transgene, permitting quick combination with other traits, such as insect or herbicide resistance.

In some aspects of the present disclosure, the nucleic acid sequences can be stacked with any combination of polynucleotide sequences of interest in order to create plants with a desired phenotype. This stacking can be accomplished by a combination of genes within a DNA construct, or by crossing one or more plants having transgenes with another plant line that comprises a desired combination. For example, the polynucleotides of the present disclosure or fragments thereof can be stacked with any other polynucleotides of the disclosure, or with other genes. The combinations generated can also include multiple copies of any one of the polynucleotides of interest. The polynucleotides of the present disclosure can also be stacked with any other gene or combination of genes to produce plants with a variety of desired trait combinations including and not limited to traits desirable for animal feed such as high oil genes, balanced amino acids, increased digestibility, insect, disease or herbicide resistance, avirulence and disease resistance genes, agronomic traits (e.g, male sterility, flowering time) and/or transformation technology traits (e.g, cell cycle regulation or gene targeting).

These stacked combinations can be created by any method including and not limited to cross breeding plants by any conventional or known methodology, or genetic transformation. If the traits are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that can suppress the expression of the polynucleotide of interest. This can be combined with any combination of other suppression cassettes or overexpression cassettes to generate the desired combination of traits in the plant.

A feature of the present disclosure are methods comprising introducing a polynucleotide into a plant. The term "introducing" as used herein refers to presenting to the plant, for example, a polynucleotide. In some aspects of the present disclosure, the polynucleotide can be presented in such a manner that the sequence gains access to the interior of a cell of the plant, including its potential insertion into the genome of a plant. The methods of the present disclosure do not depend on a particular method for introducing a sequence into a plant, only that the polynucleotide gains access to the interior of at least one cell of the plant. Methods for introducing polynucleotides into plants are known in the art including, and are not limited to, stable transformation methods, transient transformation methods, and virus-mediated methods.

The term "transformation" is used herein to mean the transfer of, for example, a nucleic acid fragment into the genome of a host organism, resulting in genetically stable inheritance. Host organisms containing the transformed nucleic acid fragments are referred to as "transgenic" organisms. The term "host cell" refers to the cell into which transformation of the recombinant DNA construct takes place and can include a yeast cell, a bacterial cell, and/or a plant cell. Examples of methods of plant transformation include Agrobacterium-mediated transformation and particle-bombardment that then can be used to regenerate a transformed plant by methods known to one skilled in the art.

A polynucleotide can be transiently or stably introduced into a host cell and can be maintained non-integrated, for example, as a plasmid. "Stable transformation" or "stably transformed" means that the nucleotide construct introduced into a plant integrates into the genome of the plant and is capable of being inherited by the progeny thereof. "Transient transformation" as used herein means that a polynucleotide is introduced into the plant and does not integrate into the genome of the plant or a polypeptide is introduced into a plant.

Transformation methods as well as methods for introducing polynucleotide sequences into plants can depend on the type of plant or plant cell, i.e., monocot or dicot, targeted for transformation. Suitable methods of introducing polypeptides and polynucleotides into plant cells include, but are not limited to, microinjection, electroporation, direct gene transfer, Lec1 transformation and ballistic particle acceleration. As newer methods become available, they can also be applied to the present disclosure as the method of transformation or transfection is not critical.

The cells that have been transformed can be grown into plants in accordance with conventional ways. These plants can then be grown, and either pollinated with the same transformed strain or different strains, and the resulting progeny having constitutive expression of the desired phenotypic characteristic identified. Two or more generations can be grown to ensure that expression of the desired phenotypic characteristic is stably maintained and inherited and then seeds harvested to ensure expression of the desired phenotypic characteristic has been achieved. In some aspects of the present disclosure, the transformed seed or transgenic seed having a nucleotide construct or an expression cassette is stably incorporated into their genome.

In an aspect, the present disclosure encompasses seeds comprising a polynucleotide sequence disclosed herein that can develop into or can be used to develop a plant or plants with increased or enhanced resistance to a pathogen (e.g., fungi) or infection caused by a pathogen as compared to, for example, a wild-type variety of the plant seed. In an aspect, the present disclosure features seeds from transgenic legume crop plants wherein the seed comprises a polynucleotide disclosed herein.

The present disclosure can be used for transformation of any plant species, including, but not limited to, monocots and dicots. Examples of plants of interest include, but are not limited to, corn (*Zea mays*), *Brassica* spp. (e.g., *Brassica napus, Brassica rapa, Brassica juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaccum*), foxtail millet (*Setaria italica*), finger millet (*Eleusine coracana*), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatas*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals, and conifers.

In an aspect, plants of interest include, a legume crop species, including, but not limited to, alfalfa (*Medicago sativa*); clover or trefoil (*Trifolium* spp.); pea, including (*Pisum sativum*), pigeon pea (*Gajanus cajan*), cowpea (*Vigna unguiculata*) and *Lathyrus* spp.; bean (Fabaceae or Leguminosae); lentil (*Lens culinaris*); lupin (*Lupinus* spp.); mesquite (*Prosopis* spp.); carob (*Ceratonia siliqua*), soybean (*Glycine max*), peanut (*Arachis hypogaea*) or tamarind (*Tamarindus indica*). The terms "legume species" and "legume crop species" are used herein to refer to plants, and can be for example, a plant of interest. In some aspects, the legume species or legume crop species is a plant, plant part or plant cell.

The term "transgenic" is used herein to refer to a plant, including any part derived from a plant, such as a cell, tissue, or organ in which an exogenous nucleic acid (e.g., recombinant construct, vector or expression cassette including one or more nucleic acids) is integrated into the genome by a genetic engineering method, such as Agrobacteria transformation. By carrying out a gene technology method, the exogenous nucleic acid is stably integrated into a chromosome, so that successive generations may also be transgenic. As used herein, "transgenic" also encompasses biological processes including the crossing of plans and/or natural recombination.

In an aspect, constructs or vectors or expression cassettes are not present in the genome of the original plant or are present in the genome of the transgenic plant, but not at their natural locus of the genome of the original plant.

The compositions disclosed herein can be generated or maintained through the process of introgressing. Introgressing is sometimes called "backcrossing" when the process is repeated two or more times. In introgressing or backcrossing, the "donor" parent refers to the parental plant with the desired gene or locus to be introgressed. The "recipient" parent (used one or more times) or "recurrent" parent (used two or more times) refers to the parental plant into which the gene or locus is being introgressed. The initial cross gives rise to the F1 generation; the term "BC1" then refers to the second use of the recurrent parent, and "BC2" refers to the third use of the recurrent parent, and so on.

Accordingly, an aspect of the present disclosure is a method of enhancing plant resistance to a plant disease, such as ASR. The method can comprise conferring resistance to a pathogen, for example, a pathogen that causes ASR, by introgression of a legume-derived NB-LRR resistance gene into germplasm in a breeding program (i.e., a breeding program for resistance to ASR).

The term "germplasm" is used herein to mean genetic material of or from an individual (e.g., a plant), a group of individuals (e.g., a plant line, variety or family), or a clone derived from a line, variety, species, or culture. The germplasm can be part of an organism or cell, or can be separate from the organism or cell. The germplasm provides genetic material with a specific molecular makeup that provides a physical foundation for some or all of the hereditary qualities of an organism or cell culture. Germplasm in the context of the present disclosure includes cells, seed or tissues from which new plants can be grown, or plant parts, such as leaves, stems, pollen, or cells, that can be cultured into a whole plant.

Aspects of the present disclosure comprise methods for identification of germplasm as a source of resistance including, but not limited to, germplasm in one or more of the following genus: *Glycine, Vigna*, and *Lablab*.

As described herein, legume-derived NB-LRR type resistance genes convey differential responses to *Phakopsora pachyrhizi*. Previous studies in six Australian races of *Phakopsora pachyrhizi* can be discerned, for example, based on their respective compatibility or incompatibility on several species of wild *Glycine* (Burdon and Marshall (1981) Journal of Ecology, 69:381-390; Burdon and Marshall (1981) Plant Disease, 65:44-45: Burdon and Speer (1984) Euphytica, 33-891-896: Burdon (1987) Ocecologia, 73(2): 257-267; Burdon (1988) Theor. Appl. Genet., 75:923-928; and Jarosz and Burdon (1990) Heredity, 64:347-353 Accordingly, in an aspect, the legume crop species or legume-derived gene is derived from the genus *Glycine*. Examples of *Glycine* species include, but are not limited to, *Glycine arenaria Glycine argyrea, Glycine cyrtoloba, Glycine canesens, Glycine clandestine, Glycine curvata, Glycine falcata, Glycine latifolia, Glycine microphylla, Glycine pescadrensis, Glycine stenophita, Glycine syndetica, Glycine soja, Glycine tabacina*, and *Glycine tomentella.*

Other genera, such as *Vigna* and *Lablab*, also display differential responses to *Phakopsora pachyrhizi*. Thus, in an aspect, the legume crop species or legume-derived gene is derived from the genus *Vigna. Vigna* is a pantropic genus that comprises approximately 100 species. It is a taxonomic group subdivided into the subgenera *Vigna, Haydonia, Plectotropis* (African), *Ceratotropis* (Asian), *Sigmoidotropis*, and *Lasiopron*. The genus includes economically relevant species such as *Vigna unguiculata* (L.) Walp (cowpea), *Vigna radiata* (L.) Wilczek (mung bean), *Vigna angularis*

(Willd.) Ohwi and Ohashi (azuki bean), *Vigna mungo* (L.) Hepper (black gram), and *Vigna umbellata* (Thunb.) Ohwi and Ohashi (rice bean). Four subspecies are recognized within *Vigna unguiculata: dekindtiana*, a wild relative of cultivated subspecies; *cylindrica*, cultivated cajang; *sesquipedalis*, cultivated yardlong bean: and *unguiculata*, cultivated black-eyed pea. *Vigna unguiculata* ssp. *unguiculata* is further divided into cultivar groups *Unguiculata*, grown as a pulse; *Biflora* or *Cilindrica* (catjang), mainly used as a forage; *Sesquipedalis* (yardlong or asparagus bean), grown as a vegetable; Textilis, cultivated for the fibres of its long floral peduncles; and Melanophthalmus (black-eyed pea). Susceptibility of several *Vigna* species, including *Vigna radiata, Vigna mungo* and *Vigna unguiculata* to *Phakopsora pachyrhizi* has been reported under field and greenhouse conditions.

In an aspect, the legume crop species or legume-derived gene is derived from the genus *Lablab*. *Lablab purpureus* (L.) Sweet (also referred to as *Dolichos benghalensis* Jacq., *Dolichos lablab* L., *Dolichos purpureus* L., *Lablab niger* Medikus, *Lablab purpurea* (L) Sweet, *Lablab vulgaris* (L.) Savi, *Vigna aristata* Piper) is a leguminous species (Verdcourt (1971) Flora of Tropical East Africa, pp. 6%-699. Crown Agents, London, UK; and Duke et al. (1981) Handbook of Legumes of World Economic Importance, pp. 102-106, Plenum Press, New York, USA and London, UK) native to Asia and Africa (Pengelly and Maass, (2001) Gen. resour. crop ev. 48; 261-272). It is commonly known as lablab bean, hyacinth bean, bonavist bean, field bean. Egyptian bean, poor man's bean, Tonga bean (English) and by at least 20 additional vernacular names. It is grown in Africa, Asia, and the Caribbean as either a pulse crop or as a green vegetable (Duke et al (1981) Handbook of Legumes of World Economic Importance, pp. 102-106, Plenum Press, New York, USA and London, UK): and Pengelly and Maass, (2001) Gen. resour. crop ev 48: 261-272) *Lablab purpureus* has been reported as an alternative host for *Phakopsora pachyrhizi* (Pérez-Hernández, (2007) Alternative hosts of *Phakopsora pachyrhizi* in the Americas: An analysis of their role in the epidemiology of Asian soybean rust in the continental U.S. M.Sc. thesis. Iowa State University. Ames, Iowa. U.S.A.; Vakili (1981) Plant Dis. 65: 817-819; and Poonpolgui and Surin, (1980) Soybean Rust Newsletter, 3: 30-31).

In an aspect, the legume crop species or legume-derived gene is derived from the genus *Cicer, Cajanus, Medicago, Phaseolus, Pisum, Pueraria*, or *Trifolium*. Examples of *Cicer* species include, but are not limited to, *Cicer ariefinum, Cicer echinospermum, Cicer reticulatum* and *Cicer pinnatifidum*. An example of the *Cajanus* species include, but is not limited to *Cajanus cajan*. Examples of the *Medicago* species include, but are not limited to, *Medicago truncatula* and *Medicago sativa*. Examples of the *Phaseolus* species include, but are not limited to, *Phaseolus vulgaris, Phaseolus lunatus, Phaseolus acutifolius* and *Phaseolus coccineus*. Examples of the *Pisum* species include, but are not limited to, *Pisum abyssinicum, Pisum sativum, Pisum elatius, Pisum fulvum, Pisum transcaucasium* and *Pisum humile*. An example of the *Pueraria* species includes, but is not limited to, *Pueraria lobata*. Examples of the *Trifolium* species include, but are not limited to, *Trifolium aureum* and *Trifolium occidentale*.

The present disclosure also comprises sequences described herein that can be provided in expression cassettes or DNA constructs for expression in the plant of interest. In an aspect, the cassette can include 5' and 3' heterologous regulator sequences operably linked to a sequence disclosed herein. The term "operatively linked" is used herein to mean that the nucleic acid to be expressed is linked to the regulatory sequence, including promoters, terminators, enhancers and/or other expression control elements (e.g., polyadenylation signals), in a manner which allows for expression of the nucleic acid (i.e., in a host plant cell when the vector is introduced into the host plant cell). Such regulatory sequences are well known in the art and include those that direct constitutive expression of a nucleotide sequence in many types of host cells and those that direct expression of the nucleotide sequence in certain host cells or under certain conditions. The design of the vector can depend on, for example, the type of the host cell to be transformed or the level of expression of nucleic acid desired. The cassette can contain one or more additional genes to be co-transformed into the plant. And, any additional gene(s) can be provided on multiple expression cassettes.

Expression cassettes of the present disclosure can include many restriction sites for insertion of the nucleotide sequence to be under the transcriptional regulation of the regulatory regions. The expression cassette can also contain selectable marker genes.

An expression cassette can further include in the 5'-3' direction of transcription, a transcriptional and translational initiation region, a DNA sequence of the disclosure, and a transcriptional and translational termination region functional in plant. The transcriptional initiation region, the promoter, can be native or analogous or foreign or heterologous to the plant host. Additionally, the promoter can be the natural sequence or alternatively a synthetic sequence. The term "foreign" means that the transcriptional initiation region is not found in the native plant into which the transcriptional initiation region is introduced. As used herein, a chimeric gene comprises a coding sequence operably linked to a transcription initiation region that is heterologous to the coding sequence. Examples of promoters include, but are not limited to, the Cauliflower Mosaic Virus 35S and soybean Ubiquitin 6.

While it may be preferable to express the sequences using heterologous promoters, homologous promoters or native promoter sequences can be used. Such constructs would change expression levels in the host cell (i.e., plant or plant cell). Thus, the phenotype of the host cell (i.e., plant or plant cell) is altered.

A termination region can be native with the transcriptional initiation region, native with the operably linked DNA sequence of interest, or derived from another source. Convenient termination regions are available from the Ti-plasmid of *Agrobacterium tumefaciens*, such as the octopine synthase and nopaline synthase termination regions.

In an aspect, endogenous or transgenic resistance orthologs can be altered by homologous or non-homologous recombinatory methods, such as, for example, by genome editing. Such alterations refer to a nucleotide sequence having at least one modification when compared to its non-modified sequence and include, for example: (i) replacement of at least one nucleotide, (ii) deletion of at least one nucleotide, (iii) insertion of at least one nucleotide, or (iv) any combination of (i)-(iii).

In some embodiments, the disclosed N-LRR polynucleotide compositions can be introduced into the genome of a plant using genome editing technologies, or previously introduced NB-LRR polynucleotides in the genome of a plant may be edited using genome editing technologies.

Genome editing can be accomplished using any gene editing method available. For example, gene editing can be achieved by introducing a polynucleotide modification template (sometimes referred to as a gene repair oligonucleotide) into a host cell, wherein the polynucleotide modification template comprises a targeted modification to a gene within the genome of the host cell. The polynucleotide modification template can be single-stranded or double-stranded. For example, see U.S. Publication No. 2013/0019349.

In some embodiments, gene editing can be carried out by inducing a double-stranded break (DSB) in a defined position in the genome near the desired alteration. DSBs can be induced using any DSB-inducing agent available, including, but not limited to, TALENs, meganucleases, zinc finger nucleases, Cas9-gRNA systems (based on bacterial CRISPR-Cas9 systems), and the like. In some embodiments, the introduction of a DSB can be combined with the introduction of a polynucleotide modification template.

The method for editing a genomic sequence can comprise combining DSB and polynucleotide modification templates and generally further comprising: 1) providing to a host cell, a DSB-inducing agent, or a nucleic acid encoding a DSB-inducing agent, wherein the DSB-inducing agent recognizes a target sequence in the chromosomal sequence, and is thereby able to induce a DSB in the genomic sequence, and 2) one or more polynucleotide modification templates comprising one or more nucleotide alterations as compared to the nucleotide sequence to be edited. The polynucleotide modification template can further comprise nucleotide sequences ranking the one or more nucleotide alterations, wherein the flanking sequences are substantially homologous to the chromosomal region flanking the DSB. Genome editing techniques using DSB-inducing agents, such as Cas9-gRNA complexes, are known in the art (see, for example, U.S. application Ser. No. 14/463,687, filed Aug. 20, 2014, PCT application PCT/US14/51781 filed Aug. 20, 2014, and U.S. application 62/036,652, filed on Aug. 13, 2014; all of which are incorporated by reference herein). Guide polynucleotide/Cas endonuclease systems are also known in the art (see, for example, U.S. application Ser. No. 14/463,691, filed Aug. 20, 2014, which is herein incorporated by reference). Additional uses for guide RNA/Cas endonuclease systems are described in U.S. application Ser. Nos. 14/463,687 and 14/463,691, filed Aug. 20, 2014, and include, but are not limited to, modifying or replacing nucleotide sequences of interest (e.g., regulatory elements), insertion of polynucleotides of interest, gene knock-out, gene-knock in, modification of splicing sites and/or introducing alternate splicing sites, modifications of nucleotide sequences encoding a protein of interest, amino acid and/or protein fusions, and gene silencing by expressing an inverted repeat into a gene of interest.

The gene(s) can be optimized for increased expression in the transformed plant as needed. In other words, the genes can be synthesized using plant-preferred codons for improved expression. Methods for synthesizing plant-preferred genes are known in the art.

Additional sequence modifications are known to enhance gene expression in a cellular host. These include elimination of sequences encoding spurious polyadenylation signals, exon-intron splice site signals, transposon-like repeats, and other such well-characterized sequences that can be deleterious to gene expression. The G-C content of the sequence can be adjusted to levels average for a given cellular host; as calculated by reference to known genes expressed in the host cell. When possible, the sequence is modified to avoid predicted hairpin secondary mRNA structures.

The expression cassettes can additionally contain 5' leader sequences in the expression cassette construct. Such leader sequences can act to enhance translation. Translation leaders are known in the art and include: picornavirus leaders, for example, EMCV leader (Encephalomyocarditis 5' noncoding region); potyvirus leaders, for example, TEV leader (Tobacco Etch Virus), and human immunoglobulin heavy chain binding protein (BiP); untranslated leader from the coat protein mRNA of alfalfa mosaic virus (AMV RNA 4); tobacco mosaic virus leader (TMV); and maize chlorotic mottle virus leader (MCMV) (Lommel et al. (1991) Virology 81:382 385). Other methods known to enhance translation can also be utilized, such as, introns.

The various DNA fragments can be manipulated while preparing the expression cassette, to ensure that the DNA sequences are in the proper orientation and, as appropriate, in the proper reading frame. Toward this end, adapters or linkers can be employed to join the DNA fragments. Alternatively, other manipulations can be used to provide for convenient restriction sites, removal of superfluous DNA, or removal of restriction sites. For this purpose, in vitro mutagenesis, primer repair, restriction, annealing, resubstitutions, e.g., transitions and transversions, can be involved.

Generally, the expression cassette can comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glyphosate, glufosinate ammonium, bromoxynil, imidazolinones, and 2,4-dichlorophenoxyacetate (2,4-D). The above list of selectable marker genes is not meant to be limiting. Any selectable marker gene can be used in the present disclosure.

For expression of a target gene and/or protein (e.g., one or more NB-LRR genes and/or one or more R proteins) of the present disclosure in a plant or plant cell, the methods described herein comprise transforming a plant or plant cell with a polynucleotide, for example, as disclosed herein, that encodes the target R protein. The polynucleotides described herein can be operably linked to a promoter that drives expression in a plant cell. Any promoter known in the art can be used in the methods of the present disclosure including, but not limited to, constitutive promoters, pathogen-inducible promoters, wound-inducible promoters, tissue-preferred promoters, and chemical-regulated promoters. The choice of promoter may depend on the desired timing and location of expression in the transformed plant as well as other factors, which are known to those of skill in the art. Transformed cells or plants can be grown or bred to generate a plant comprising one or more of polynucleotides that were introduced into the cell or plant that, for example, encodes an R protein.

A number of promoters can be used in the practice of the disclosure. The promoters can be selected based on the desired outcome. That is, the nucleic acids can be combined with constitutive, tissue-preferred, or other promoters for expression in the host cell of interest. Such constitutive promoters include, for example, the core promoter of the Rsyn7 promoter and other constitutive promoters disclosed in WO 99/43838 and U.S. Pat. No. 6,072,050; the core CaMV 35S promoter, rice actin; ubiquitin; pEMU; MAS; ALS; and the like. Other constitutive promoters include, for example, those disclosed in U.S. Pat. Nos. 5,608,149; 5,608,144; 5,604,121; 5,569,597; 5,466,785; 5,399,680; 5,268, 463; 5,608,142; and 6,177,611, which are known in the art, and can be contemplated for use in the present disclosure.

Generally, it can be beneficial to express the gene from an inducible promoter, particularly from a pathogen-inducible promoter. Such promoters include those from pathogenesis-related proteins (PR proteins), which are induced following infection by a pathogen, e.g., PR proteins. SAR proteins, beta-1,3-glucanase, chitinase, etc.

Of interest are promoters that are expressed locally at or near the site of pathogen infection. Additionally, as pathogens find entry into plants through wounds or insect damage, a wound-inducible promoter can be used in the constructions of the disclosure Such wound-inducible promoters include potato proteinase inhibitor (pin 11) gene, wun1 and wun2, win1 and win2, systemin, WIP1, MPI gene, and the like.

Chemical-regulated promoters can be used to modulate the expression of a gene in a plant through the application of an exogenous chemical regulator. Depending upon the objective, the promoter can be a chemical-inducible promoter, where application of the chemical induces gene expression, or a chemical-repressible promoter, where application of the chemical represses gene expression. Chemical-inducible promoters are known in the art and include, but are not limited to, the maize In2-2 promoter, which is activated by benzenesulfonamide herbicide safeners, the maize GST promoter, which is activated by hydrophobic electrophilic compounds that are used as pre-emergent herbicides, and the tobacco PR-1a promoter, which is activated by salicylic acid. Other chemical-regulated promoters of interest include steroid-responsive promoters (e.g., the glucocorticoid-inducible promoter, and tetracycline-inducible and tetracycline-repressible promoters).

Tissue-preferred promoters can be utilized to target enhanced expression of the target gene or protein (e.g., a polynucleotide sequence encoding a legume-derived NB-LRR polypeptide) within a particular plant tissue. Such tissue-preferred promoters include, but are not limited to, leaf-preferred promoters, root-preferred promoters, seed-preferred promoters, and stem-preferred promoters. Tissue-preferred promoters include Yamamoto et al. (1997) Plant J. 12(2):255-265; Kawamata et al. (1997) Plant Cell Physiol. 38(7):792-803; Hansen et al, (1997) Mol. Gen Genet. 254 (3):337-343; Russell et a. (1997) Transgenic Res. 6(2):157-168; Rinehart et al, (1996) Plant Physiol. 112(3):1331-1341. Van Camp et al. (1996) Plant Physiol. 112(2):525-535; Canevascini et al. (1996) Plant Physiol. 112(2):513-524; Yamamoto et al. (1994) Plant Cell Physiol. 35(5):773-778; Lam (1994) Results Probl. Cell Differ. 20:181-196; Orozco et al. (1993) Plant Mol Biol. 23(6):1129-1138; Matsuoka et al. (1993) Proc Natl. Acad. Sci. USA 90(20):9586-9590; and Guevara-Garcia et al. (1993) Plant J. 4(3):495-505. Such promoters can be modified.

Leaf-specific promoters am known in the art. See, for example, Yamamoto et al. (1997) Plant J. 12(2):255-265; Kwon et a, (1994) Plant Physiol. 105:357-67: Yamamoto et al. (1994) Plant Cell Physiol. 35(5):773-778; Gotor et al. (1993) Plant J. 3:509-18; Orozco et al. (1993) Plant Mol. Biol. 23(6):1129-1138; and Matsuoka et al. (1993) Proc. Natl. Acad. Sci. USA 90(20):9586-9590.

"Seed-preferred" promoters include both "seed-specific" promoters (those promoters active during seed development such as promoters of seed storage proteins) as well as "seed-germinating" promoters (those promoters active during seed germination). Such seed-preferred promoters include, but are not limited to, Cim1 (cytokinin-induced message), cZ19B1 (maize 19 kDa zein), milps (myo-inositol-1-phosphate synthase), and celA (cellulose synthase) (see WO 0/11177, herein incorporated by reference). Gamazein is a preferred endosperm-specific promoter. Glob-1 is a preferred embryo-specific promoter. For dicots, seed-specific promoters include, but are not limited to, bean, β-phaseolin, napin, β-conglycinin, soybean lectin, cruciferin, and the like. For monocots, seed-specific promoters include, but are not limited to, maize 15 kDa zein, 22 k Da zein, 27 kDa zein, g-zein, waxy, shrunken 1, shrunken 2, globulin 1, etc. See also WO 00/12733, where seed-preferred promoters from end1 and end2 genes are disclosed; herein incorporated by reference.

Expression of the polynucleotides of the present disclosure can involve the use of the intact, native R gene, wherein the expression is driven by a cognate 5' upstream promoter sequence. Alternatively, expression can be generated using constructs assembled with 5' transcriptional control sequences provided by heterologous NB-LRR disease resistance genes expressed in the host legume. One skilled in the art will be able to identify genes encoding NB-LRR proteins, to evaluate their expression level, and to select preferred promoter sequences that can be used for expression of the R gene of interest. The use of either cognate or heterologous NB-LRR promoter sequences provides an option to regulate protein expression to avoid or minimize any potential undesired outcomes associated with inappropriate or unwanted expression and plant defense activation.

Specific soybean promoters include but are not limited to soy ubiquitin (subi-1), elongation factor 1A, and S-adenosyl methionine synthase for constitutive expression and Rpp4, RPG1-B, and promoters contained in gene models such as Glyma promoters known to those of skill in the art for more tightly regulated expression provided by NB-LRR gene promoters.

Figure 2A:
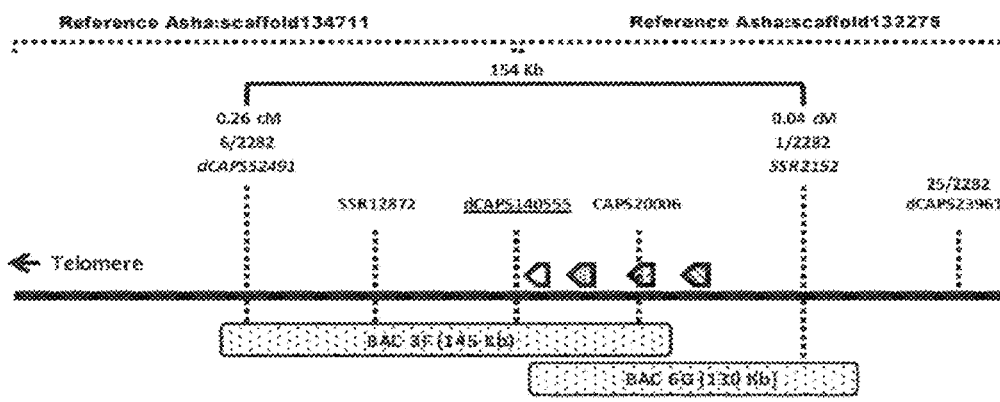
FIG. 2A-2B illustrates the physical and high-resolution genetic map interval of the CcRpp1 locus (FIG. 2A) and four NB-LRR paralog genes that were identified (FIG. 2B). The CcRpp1 genomic region in the accession G119-99 contained four NB-LRR paralogs (FIG. 2A). The R gene region was narrowed down to a region of 154 Kb encompassing markers dCAPS52491 and SSR2152. They were the most informative recombinants obtained after screening 1.141 segregating F2 plants (2282 gametes). The gain-of-function interval was delineated by the markers dCAPS52491 and dCAPS239615 and the loss-of-function interval was delineated by the markers dCAPS52491 and SSR2152. BAC 3F carried three paralogs (−1, −2 and −3) and BAC 6G carried four paralogs (−1 to −4) (FIG. 2B). The most closely linked marker dCAPS140555 was designed from the Q calmodulin-binding motif containing gene.
Figure 2B:
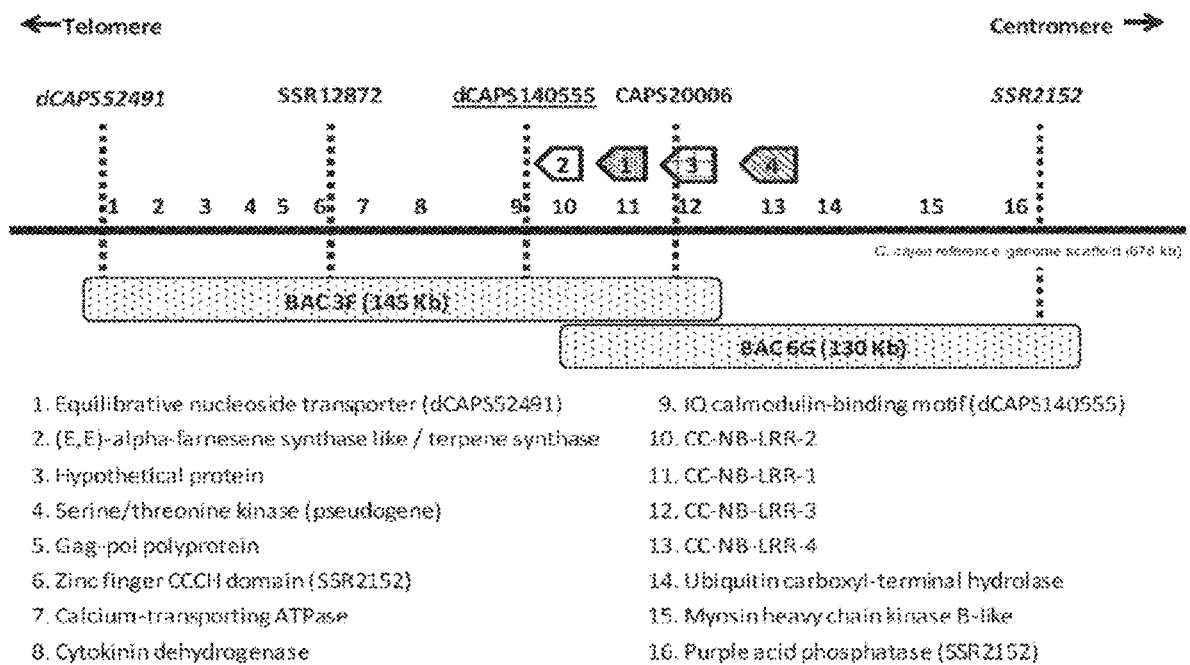

The present disclosure also includes kits for the assays described herein. The polypeptide sequences and polynucleotides can be packaged as a component of a kit with instructions for completing the assay disclosed herein. The kits of the present disclosure can include any combination of the polypeptides and/or polynucleotides described herein and suitable instructions (written and/or provided as audio-, visual-, or audiovisual material). In one embodiment, the kit relates to a DNA detection kit for identifying R genes (e.g., NB-LRR genes) or R proteins against ASR. Kits utilizing any of the sequences disclosed herein for the identification of a transgenic event (e.g, CcRpp1) in a plant for efficacy against ASR are provided. For example, the kits can comprise a specific probe having a sequence corresponding to or is complementary to a sequence having between 80% and 100% sequence identity with a specific region of the transgenic event. The kits can include any reagents and materials required to carry out the assay or detection method.

EXAMPLES

Example 1: Mapping and Cloning of CcRpp1

Screening germplasm of non-*Glycine* species for variation in susceptibility to *Phakopsora pachyrhizi*. Accessions of pigeon pea (*Cajanus cajan*) in Brazil that were originally obtained from ICRISAT and introduced into Brazil, Which had already been selected for desirable agronomic traits (Godoy at al. (2005) Rev. Bras. Zootec; 34:7-19; and Provazi et al. (2007) Rev. Bras. Zootec; 36:328-334), were screened. *Canjanus cajan* is a diploid legume, with a genome size of approximately 830 Mbp (Varshney et al. (2012) Nat. Biotechnol., 30:83-89), is self-fertile and has a life cycle between 2-3 months seed-to-seed.

The differential reaction of these accessions to *Phakopsora pachyrhizi* permitted the identification of resistant and susceptible accessions (Noriega, (2007) Resistência do plantas hospedeiras e identificação de genes diferencialmente expressos na interação soja—*Phakopsora pachyrhizi*. M.Sc. Thesis. Universidade Federal de Viçosa. Viçosa. Brazil). Plants from resistant accessions were crossed with those for the susceptible accessions, and the resulting F1 plants were self-pollinated. The resulting F2 progenies were screened for resistance and susceptibility. The CcRpp (*Cajanus cajan* resistance against *Phakopsora pachyrhizi*) genes from genotypes 0119-99 (the source of the resistance gene CcRpp1), 059-95, G146-97, G108-99, 0127-97 and G184-97 were selected for further characterization. Differential responses of several *Cajanus cajan* accessions against *Phakopsora pachyrhizi* isolate PPUFV02 were measured. The reactions ranged from resistant, partially resistant with flecks, reddish-brown lesions without sporulation, reddish-brown lesions with sporulation to susceptible with "tan" lesions with abundant sporulation on the abaxial leaflet side. The resistance of this genotype 0119-99 segregated 3:1 in the F2 population indicating that it is governed by a single dominant gene. 0108-99 was the exception, and displayed a 15:1 segregation ratio in the F2 indicating that two R genes may provide resistance.

The CcRpp1 genetic region in *Cajanus cajan*. In order to genetically map the CcRpp1 locus, mRNA was extracted from bulks of 50 susceptible and 50 resistant *Cajanus cajan* F2 plants from the cross G119-99 x G48-95. SMART™ kit and SMARTIV patented oligonucleotide (Clontech) were used for the first strand cDNA synthesis. A duplex-specific nuclease approach was employed to normalize the cDNA generated from both resistant and susceptible bulks in order to facilitate the identification and analysis of rare transcripts and to enhance the gene discovery rate of the cDNA libraries (Zhulidov et al. (2004) Nucleic Acids Res 32: e37; and Zhulidov et al. (2005) Bioorg Khim. 31: 186-94). The normalized cDNAs were then digested with SfiI and size fractionated by CHROMA spin-1000 columns to select for transcript fragments above 1 Kb. Resistant and susceptible bulked cDNAs were subsequently sheared using a Covaris S20 to obtain average fragment sizes of 200 bp. These sheared cDNAs were used to generate libraries that were sequenced with the Illumina GA2 sequencer.

Several single nucleotide polymorphisms were identified between the susceptible and resistant cDNA bulks that were linked to CcRpp1 locus. These polymorphisms were used to generate markers for fine mapping. Marker dCAPS140555 was linked to the CcRpp1 locus in 2282 gametes analyzed (1141 F2 plants).

Since no reference *Cajanus cajan* genome was available at the time the mapping data was generated, synteny analyses of *Cajanus cajan* with *Medicago truncatula* and *Glycine max* were performed. To this end, sequences from seven markers genetically linked to CcRpp1 were aligned against the *Medicago truncatula* genome (*Medicago truncatula* sequencing resources-Mt3.0) and to the *Glycine max* genome (Phytozome v5.0) using the BLAST algorithm. *Glycine max* is an ancient allotetraploid and chromosomes 9 and 12 are homologous. Interestingly, the seven linked markers identified in *Cajanus cajan* displayed strong synteny with two regions in the *Glycine max* genome; one on chromosome 12, and one on chromosome 9. A homologous region on chromosome 4 of *Medicago truncatula* was also identified. To identify additional polymorphisms and indels for marker development, a 2 Mb region starting from the telomere region on chromosome 12 that contains the identified homologous region was used as a reference. This reference was used for alignment of the transcriptome Illumina data from the *Cajanus cajan* resistant parental accession 0119-99 reads combined with the reads generated from the resistant bulk of 50 $F_2$ lines and aligned against the reads obtained from the susceptible bulk. Using this approach, five polymorphic and indel sequences were obtained which provided extra markers for fine mapping of CcRpp1 (dCAPS3978, SSR10581, dCAPS52491, SSR2152, dCAPS239615; FIG. 1). The majority of these marker sequences were located within a 1.5 Mb region on chromosome 12 of *Glycine max*. Notably, the dCAPS140555 marker (so far linked to CcRpp1 gene in *Cajanus cajan*) is located 6 Kb from a classical CC-NB-LRR gene in *Glycine max* (Glyma12g01420) and situated in a 106 Kb genetic interval delimited by the dCAPS52491 and SSR2152 marker sequences (FIG. 1).

Sequencing of a BAC clone from the reference *Cajanus cajan* vanity "Asha" reveals that the CcRpp1 locus contains one or more genes from the NB-LRR gene family. To this end, the BAC library was screened from the sequenced reference variety "Asha" (Varshney et al. (2009) Nat. Biotechnol., 30:83-89) using a probe derived from marker dCAPS140555 and identified a BAC clone of 97 Kb. This clone was sheared to obtain average fragment sizes of 5 Kb that were sequenced using Sanger sequencing. The reads were subsequently assembled using Phred, Phrap and Consed data analyses. Sequence annotation of this BAC revealed the presence of four highly homologous NB-LRR gene paralogs, three full-length genes and one truncated gene.

High-resolution mapping reveals that CcRpp1 is located between the markers dCAPS52491 and SSR2152 and very tightly linked to dCAPS140555. The CcRpp1 locus was mapped to chromosome 5 in G119-99 using more than 1141 individual F2 plants with SSRs, CAPs and dCAPs markers. The region containing CcRpp1 was narrowed down to a region of <154 Kb encompassing the dCAPS52491 (6 recombinants/2282 gametes) and SSR2152 (1 recombinant/2282 gametes) markers (FIG. 2A). These markers are tightly linked to CcRpp1 with dCAPS52491 and SSR2152 being, 0.26 cM and 0.04 cM, respectively, away from the R gene locus (FIG. 2A). Flanking the markers dCAPS52491 and SSR12872, two gain-of-function recombinants were observed, and flanking the markers CAPS20006 and SSR2152, 1 loss-of-function recombinant was observed. Therefore the gain-of-function interval was delineated by the markers dCAPS52491 and dCAPS239615 and the loss-of-function interval was delineated by the markers dCAPS52491 and SSR2152 (FIG. 2A), demonstrating that CcRpp1 locus was located in the region that contains the NB-LRR genes.

Example 2: CcRpp1 Locus from G119-99 Contains Four Members of a NB-LRR Family In order to determine the genomic organization of the CcRpp1 locus in G119-99, a G119-99 BAC library was generated and screened using two probes derived from markers dCAPS140555 and SSR2152, respectively. Two positive BAC clones (3F and 60) were identified that together span the entire interval between dCAPS52491 and SSR2152 (FIG. 2B). Several clones containing BAC 3F (145 Kb) and BAC 6G (130 Kb) were tested for integrity via DNA fingerprinting using the restriction enzyme HindIII. In addition, the BAC sizes of these clones were verified by pulse-field gel electrophoresis of NofI-digested DNA. One clone from each 3F and 60 that passed the above quality control was sequenced with PacBio and Illumina MiSeq to enable rapid and accurate assembly of each BAC sequence (Koren et al. (2012) Nature Biotechnology 30:693-970). The two BAC sequences were assembled into one large contig of 205.344 Kb (FIG. 2B). Four NB-LRR candidate gene sequences were identified in this contig: BAC 3F carries 3 of the NB-LRR gene sequences, NB-LRR-1, -2 and -3, (SEQ ID NOs: 3, 1, and 5, respectively) and BAC 6G carries 4 NB-LRR gene sequences, NB-LRR-1 to -4, (SEQ 1 NOs: 3, 1, 5 and 7) Using the transcriptome Illumina data from the non-challenged G119-99 genotype, only the de novo assembly with Trinity the full-length transcript of NB-LRR-2 was found. Southern blot analysis showed that the CcRpp1 locus in G119-99 contains four members of a NB-LRR gene family, corroborating the BAC gene annotation.

Example 3: Transformation of Soybean with the *Cajanus Cajan* N-LRR-2 Gene (SEQ ID NO: 1)

A plant transformation construct was designed to provide high-level constitutive expression of NB-LRR-2, (SEQ ID NO: 1) in soybean. A 2775 bp SfiI fragment containing the NB-LRR-2 coding region was ligated at the 5' end to a 1948 bp soybean ubiquitin promoter+IntronI fragment and on the 3' end to a 888 bp *Arabidopsis* ubiquitin terminator fragment. The entire promoter-coding region-terminator cassette was located between attR1 and attR2 recombination sites in a Gateway® based plant expression vector. This vector, in addition to the above elements, contained a hygromycin resistance gene for bacterial selection and an herbicide resistant soybean ALS gene as a plant selectable marker.

The final NB-LRR-2 plant expression vector was electroporated into *Escherichia coli*. Transformants were then selected and pDNA were isolated by standard miniprep methods. Transformants were characterized by diagnostic restriction enzyme digestions of miniprep DNA A positive clone containing the expected pattern of digestion bands was selected, and isolated DNA was submitted for biolistic transformation.

Biolistic transformation of soybean. Transgenic soybean lines were generated by the method of particle gun bombardment (U.S. Pat. No. 4,945,050) using a BIORAD Biolistic PDS1000/He instrument and either plasmid or fragment DNA. The following stock solutions and media were used for transformation and regeneration of soybean plants.

Stock solutions: Sulfate 100× Stock (37.0 g $MgSO_4.7H_2O$, 1.69 g $MnSO^4.H^2O$, 0.86 g $ZnSO^4.7H_2O$, 0.0025 g $CuSO_4$ $5H_2O$); Halides 100× Stock (300 g $CaCl_2.2H_2O$, 0.083 g KI, 0.0025 g $CoCl_2.6H2O$); P, B, Mo 100× Stock (18.5 g $KH_2PO_4$, 0.62 g $H_3BO_3$, 0.025 g $Na_2MoO_4.2H_2O$); Fe EDTA 100× Stock (3.724 g $Na_2EDTA$, 2.784 g $FeSO_40.7H_2O$); 2,4 D Stock (10 mg/mL) and B5 vitamins, 1000× Stock (100.0 g myo-inositol, 1.0 g nicotinic acid, 1.0 g pyridoxine HCl, and 10 g thiamine HCL.

Media (per Liter): SB199 Solid Medium (1 package MS salts (Gibco/BRL; Cat. No. 11117-066), 1 ml. 85 vitamins 1000× stock, 30 g Sucrose, 4 ml 2, 4-D (40 mg/L final concentration). pH 7.0, 2 gm Gelrite); SB1 Solid Medium (I package MS salts (Gibco/BRL; Cat. No. 11117-066), 1 mL B5 vitamins 1000× stock, 31.5 g Glucose, 2 mL 2,4-D (20 mg/L final concentration), pH 5.7, 8 g TC agar); SB196 (10 mL of each of the above stock solutions 1-4, 1 mL B5 Vitamin stock, 0.463 g $(NH_4)^2$ $SO_4$, 2.83 g $KNO_3$, 1 mL 2,4-D stock, 1 g Asparagine, 10 g Sucrose, pH 5.7); SB71-4 (Gamborg's B5 salts. 20 g sucrose, 5 g TC agar, pH 5.7); SB103 (1 pk. Murashige & Skoog salts mixture. 1 mL B5 Vitamin stock, 750 mg $MgCl_2$ hexahydrate, 60 g maltose, 2 g Gelrite™, pH 5.7); and SB166 (SB103 supplemented with 5 g per liter activated charcoal).

Soybean embryogenic suspension culture initiation. Pods with immature seeds from available soybean plants 45-55 days after planting were picked, removed from their shells and placed into a sterilized magenta box. The soybean seeds were sterilized by shaking them for 15 min in a 5% Clorox® solution with 1 drop of Ivory™ soap (i.e., 95 mL of autoclaved distilled water plus 5 mL Clorox® and 1 drop of soap, mixed well). Seeds were rinsed using 2 L sterile distilled water and those less than 3 mm were placed on individual microscope slides. The small end of the seed was cut and the cotyledons pressed out of the seed coat. Cotyledons were transferred to plates containing SB199 medium (25-30 cotyledons per plate) for 2 weeks, then transferred to SB1 for 2-4 weeks. Plates were wrapped with fiber tape. After this time, secondary embryos were cut and placed into SB1% liquid medium for 7 days.

Culture conditions. Soybean embryogenic suspension cultures were maintained in 50 mL liquid medium S196 on a rotary shaker, 100-150 rpm, 26° C. on 16:8 h day/night photoperiod at light intensity of 80-100 $\mu E/m^2/s$. Cultures were subcultured every 7-14 days by inoculating up to M dime size quantity of tissue (clumps bulked together) into 50 mL of fresh liquid SB1%.

Preparation of DNA for bombardment. In particle gun bombardment procedures, it is possible to use either purified entire plasmid DNA or DNA fragments containing only the recombinant DNA expression cassette(s) of interest. For every seventeen bombardment transformations, 85 µL of suspension was prepared containing 1 to 90 picograms (pg) of plasmid DNA per base pair of each DNA plasmid. DNA plasmids or fragments were co-precipitated onto gold particles as follows. The DNAs in suspension were added to 50 µL of a 10-60 mg/mL 0.6 µm gold particle suspension and then combined with 50 µL $CaCl_2$ (2.5 M) and 20 µL spermidine (0.1 M) The mixture was vortexed for 5 sec, spun in a microfuge for 5 see, and the supernatant removed. The DNA coated particles were then washed once with 150 µL of 100% ethanol, vortexed and spun in a microfuge again, then resuspended in 85 µL of anhydrous ethanol. Five microliters of the DNA coated gold particles were then loaded on each macrocarrier disk.

Tissue preparation and bombardment with DNA. Approximately 100 mg of two-week-old suspension culture was placed in an empty 60 mm×15 mm petri plate and the residual liquid removed from the tissue using a pipette. The tissue was placed about 3.5 inches away from the retaining screen and each plate of tissue was bombarded once. Membrane rupture pressure was set at 650 psi and the chamber was evacuated to −28 inches of Hg. Following bombardment, the tissue from each plate was divided between two flasks, placed back into liquid media, and cultured as described above.

Selection of transformed embryos and plant regeneration. After bombardment, tissue from each bombarded plate was divided and placed into two flasks of SB196 liquid culture maintenance medium per plate of bombarded tissue. Seven days post bombardment, the liquid medium in each flask was replaced with fresh SB196 culture maintenance medium supplemented with 100 ng/ml selective agent (selection medium). For selection of transformed soybean cells, the selective agent used was a sulfonylurea (SU) compound with the chemical name, 2 chloro N ((4 methoxy 6 methy 1.35 triazine 2 yl) aminocarbonyl) benzenesulfonamide (other common names are DPX-W4189 and chlorsulfuron).

Chlorsulfuron is the active ingredient in the DuPont sulfonylurea herbicide, GLEAN®. The selection medium containing SU was replaced every two weeks for 8 weeks. After the 8 week selection period, islands of green transformed tissue were observed growing from untransformed, necrotic embryogenic clusters. These putative transgenic events were isolated and kept in SB196 liquid medium with SU at 100 ng/ml for another 5 weeks with media changes every 1-2 weeks to generate new, clonally propagated, transformed embryogenic suspension cultures. Embryos spent a total of around 13 weeks in contact with SU. Suspension cultures were sub-cultured and maintained as clusters of immature embryos and also regenerated into whole plants by maturation and germination of individual somatic embryos.

Somatic embryos became suitable for germination after four weeks on maturation medium (1 week on SB166 followed by 3 weeks on SB103). They were then removed from the maturation medium and dried in empty petri dishes for up to seven days. The dried embryos were then planted in SB714 medium where they were allowed to germinate under the same light and temperature conditions as described above. Germinated embryos were transferred to potting medium and grown to maturity for seed production.

Example 4: Testing Transgenic Plants for Efficacy Against ASR

The NB-LRR-2 gene was tested for efficacy against ASR by transformation of plant expression constructs into soybean, followed by inoculation of transgenic plants with *Phakopsora pachyrhizi* and scoring of plant disease symptoms.

A total of 3 transgenic events were recovered from the soy transformation experiment and confirmed by qPCR to contain the NB-LRR-2 gene (SEQ ID NO: 1). All 3 events were additionally shown by RT-PCR to express a diagnostic 543 bp fragment of the NB-LRR-2 transcript.

Preliminary testing of primary transformants was performed to evaluate the effect of the NB-LRR-2 transgene on ASR infection. To this end, T0 plant material was spray-inoculated with $1 \times 10^5$ spores/ml of *Phakopsora pachyrhizi*. Inoculated material from control source plants and T0 transgenic plants was incubated and scored for disease symptoms 12 days after inoculation. Plants were visually assessed for the presence of lesions and microscopically evaluated to detect the presence of uredinia.

No sporulation was observed on leaves from three plants representing two independent events (5.1 and 7.1) that were confirmed to express full length NB-LRR-2, interestingly, one transgenic event (6.1) displayed full susceptibility to ASR and contained tan, heavily sporulating lesions. Further analyses revealed, that in this particular transformant, the integrity of the inserted DNA was compromised, leading to synthesis of a truncated transcript, thus precluding expression of NB-LRR-2 in this plant. Since NB-LRR-2 is able to provide resistance against *Phakopsora pachyrhizi* in Events 5.1 and 7.1, NB-LRR-2 was renamed CcRpp1 for *Cajanus cajan* resistance against *Phakopsora pachyrhizi* 1 and both Event 5.1 and Event 7.1 were advanced for further testing in T1 plants.

T1 transgenic testing for efficacy of CcRpp1 against *Phakopsora pachyrhizi*. Seeds from selected T1 events were planted and grown under growth chamber conditions for 17 days until VC The plants were sampled for qPCR to determine the transgene copy number and inoculated with a suspension of *Phakopsora pachyrhizi* spores. The inoculation was performed with urediniospores collected from a susceptible variety and stored at −80° C. After retrieving from storage, the spores were suspended in an aqueous solution of 0.01% Tween 20, heat-shocked at 40° C. for 5 min and mixed thoroughly; the spore concentration was then adjusted to $2 \times 10^4$ sp/ml with a hemocytometer. Plants were spray-inoculated with the urediniospore suspension, incubated at 100% relative humidity in the dark for 24 hours and then transferred to a growth chamber (22° C., 70% RH, 16 hr photoperiod) where they were allowed to grow and develop symptoms for 15-29 days. New growth was excised regularly in order to keep the unifoliates for the duration of the experiment.

In order to assess the effect of CcRpp1, plants were scored qualitatively as Resistant (R; no lesions), Partially Resistant (PR; red-brown (RB), low sporulating lesions) and Susceptible (S; tan, highly sporulating lesions) and quantitatively, by excising and scanning leaves followed by determination of lesion counts. Most null samples were scored 15 days after inoculation, while the hemizygous and homozygous plants were scored 29 days after inoculation. In order to determine the effect of the gene, the transgenic plants were compared to the null plants from the same event.

ASR infection assay results were summarized in Table 1. These results showed that CcRpp1 in homozygous samples provided resistance to ASR Lesions were rarely found; when averaged across all of the homozygous plants, there was >99% reduction in lesion counts per leaf area unit (cm$^2$). Hemizygous plants displayed partial resistance, red-brown lesions and showed 55-70% reduction in lesion count per cm$^2$. Null plants contained tan, highly sporulating lesions, typical of a susceptible reaction to the pathogen.

These ASR infection assay results show that the CcRpp1 gene was able to provide resistance to *Phakopsora pachyrhizi* when transgenically transferred from the host legume. *Cajanus cajan* to *Glycine max* plants.

TABLE 1

Measured traits for two events carrying CcRpp1. Zygosity was used as transgene copy number (null = 0, hemiz = 1, homoz = 2); R = resistant, PR = partial resistance, S = susceptible; Avg LC/cm$^2$ average lesion count per area unit (cm$^2$).

| Event | Zygosity | n | Reaction | Lesion type | Avg(LC/cm$^2$) |
|---|---|---|---|---|---|
| 5.1 | Homoz | 10 | R | Resistant | 0.01 |
|  | Hemiz | 26 | PR | RB, low sporulation | 3.79 |
|  | Null | 16 | S | Tan | 8.92 |
| 7.1 | Homoz | 27 | R | Resistant | 0.01 |
|  | Hemiz | 48 | PR | RB, low sporulation | 2.83 |
|  | Null | 30 | S | Tan | 9.5 |

Example 5: Identification of an ASR Resistance Gene in the *Cajanus Cajan* Accession G108-99

Two hundred ninety-two F2 plants from population CG 8-1 (G48-95 x G108-99) were screened with isolate PPUFV01. After inoculation. 266 plants were classified as resistant and 24 as susceptible. This observed segregation ratio suggested the presence of two independent dominant loci. Using markers 101581 and 239615 that flank the CcRpp1 locus. 53 resistant plants homozygous for the susceptible allele at CcRpp1 locus were selected. These selected F2 plants were selfed to obtain F3 seeds. Resistance segregation that is independent of the CcRpp1 locus was observed in a number of F2:3 families confirming the presence of a new resistance locus in the accession G108-99. This accession was sequenced with Illumina HiSeq2000

(20× coverage) and this data was used to identify 84535 single nucleotide polymorphisms (SNPs) between G108-99 and the susceptible parental accession (48-95 (sequenced previously). SNP genotyping using the Sequenom MassARRAY® iPLEX platform identified a region associated with the novel resistance in G108-99. It is within the scope of the present disclosure that these resistant plants serve as sources to identify R genes that confer resistance against *Phakopsora pachyrhizi*. Symptomatic accessions can be used for generating the segregating populations required to map and clone the genes conferring resistance to *Phakopsora pachyrhizi* in the corresponding resistant accessions.

Example 6: Identification of Germplasm as a Source of Resistance in the Genus *Vigna*

A total of 89 *Vigna* accessions obtained from different sources were screened with mono-pustule isolate PPUFV02. Initially, 55 accessions of *Vigna unguiculata* that were obtained from Brazilian breeding programs (Table 2) were screened. Challenging these accessions with mono-pustule isolate PPUFV02 permitted the identification of three resistant accessions and several accessions that developed disease symptoms. A notable exception was Vu32, which also developed disease symptoms in mature leaves. In several experiments, accessions Vu3, Vu7 and Vu21 consistently showed resistance to *Phakopsora pachyrhizi*. The screening of 16 additional accessions of *Vigna unguiculata* obtained from USDA-GRIN revealed plants of accessions Vun_00002, Vun_00008, Vun_00094, Vun_00095 and Vun_00145 that showed resistance whereas Vun_00001 and Vun_00135 showed lack of resistance (Table 3). Next, 18 accessions of diverse *Vigna* species obtained from AusPGRIS were screened. The latter set included seven accessions of *Vigna unguiculata*, two accessions of each *Vigna dalzelliana* and *Vigna oblongifolia*, and one accession of each *Vigna parkeri*, *Vigna filicaulis* var. Filicaulis, *Vigna kirkii*, *Vigna luteola*, *Vigna radiata*, *Vigna trilobata*, and *Vigna* sp. Accessions ARG 88 (*Vigna luteola*), ATF 2361. ATF 2364 (*Vigna oblongifolia*), ATF 2073 (*Vigna* sp.), AJP 004 (*Vigna parkeri*), and CP 121683 (*Vigna unguiculata*) developed strong disease symptoms. In contrast, accessions ATF 2783 (*Vigna dalzelliana*), ATF 2363 (*Vigna unguiculata*) and NI 456 (*Vigna unguiculata* ssp. *mensensis*) were resistant to the disease.

It is within the scope of the present disclosure that accessions Vu3, Vu7, Vu21, Vun_00002, Vun_00008, Vun_00094, Vun_00095, Vun_00145, ATF 2783. ATF 2363, and NI 456 serve as sources to identify R genes that confer resistance against *Phakopsora pachyrhizi*. Symptomatic accessions Vu32. Vun_00001, Vun 00135, ARG 88, ATF 2361, ATF 2364, ATF 2073, AJP 004, and CPI 121683 can be used for generating the segregating populations required to map and clone the genes conferring resistance to *Phakopsora pachyrhizi* in the corresponding resistant accessions. F1 populations have been obtained from crossing *Vigna* accessions with contrasting phenotypes. F2 populations from crosses Vun_00135 x Vun_00094 and Vu32 x Vu21 segregate in a 3:1 ratio, indicating that similar to *Cajanus cajan* resistance, resistance in *Vigna unguiculata* was conveyed by dominant resistance loci.

TABLE 2

Sources of resistance *Phakopsora pachyrhizi* PPUFV02 in *Vigna unguiculata* accessions from Brazil. Disease symptoms were rated using a scale ranging from 0 (resistant) to 4 (lack of resistance) according to lesion size and leaf area affected.

| Accession | Genotype | Disease Symptoms Score |
|---|---|---|
| Vu 21 | MNC99-537F-1 | 0 |
| Vu 3 | MNC99-507G-8 | 0 |
| Vu 40 | Vita-7 | 0 |
| Vu 5 | MNC99-510G-8 | 0 |
| Vu 7 | TE97-309G18 | 0 |
| Vu 6 | MNC99-510F-16 | 0 |
| Vu 22 | MNC99-537F-4 | 0 |
| Vu 1 | MNC99-505G-11 | 1 |
| Vu 15 | MNC99-542F-5 | 1 |
| Vu 17 | MNC99-547F-2 | 1 |
| Vu 18 | BRS Paraguaçu | 1 |
| Vu 19 | BR 17 Gurguéia | 1 |
| Vu 20 | CHCx 409-11F-P-2 | 1 |
| Vu 23 | MNC99-541F-5 | 1 |
| Vu 24 | MNC99-541F-8 | 1 |
| Vu 29 | MNC00-544D-10- | 1 |
| Vu 35 | MNC-01-649E-2 | 1 |
| Vu 4 | MNC99-508G-1 | 1 |
| Vu 8 | TE97-304G-4 | 1 |
| Vu 38 | BRS Guariba | 1 |
| Vu 41 | BR2-Bragnança | 1 |
| Vu 47 | BRS-Rouxinol | 1 |
| Vu 55 | Consebiola | 1 |
| Vu 56 | IPA206 | 1 |
| Vu 10 | TE97-309G-24 | 2 |
| Vu 13 | MNC99-541F-18 | 2 |
| Vu 14 | MNC99-541F-21 | 2 |
| Vu 16 | MNC99-542F-7 | 2 |
| Vu 25 | IT93K-93-10 | 2 |
| Vu 26 | Pretinho | 2 |
| Vu 27 | Fradinho-2 | 2 |
| Vu 28 | MNC99-519D-I-1 | 2 |
| Vu 35 | MNC-01-649E-2 | 2 |
| Vu 37 | MNC99-557F-2 | 2 |
| Vu 52 | MNC01-649E-1 | 2 |
| Vu 59 | Paulistinha | 2 |
| Vu 9 | TE97-304G-12 | 2 |
| Vu 39 | Patativa | 2 |
| Vu 44 | BRS-Unibuquara | 2 |
| Vn 48 | EPACE-10 | 2 |
| Vu 50 | CNCx689-128F | 2 |
| Vu 51 | MNC99-510-16-6-1 | 2 |
| Vu 58 | BR10 Piaui | 2 |
| Vu 54 | Azul | 2 |
| Vn 58 | Pele de Moça | 2 |
| Vn 12 | MNC99-541F-15 | 4 |
| Vu 2 | MNC99-507G-1 | 4 |
| Vu 31 | MNC00-553D-8-1- | 4 |
| Vu 33 | MNC00-561G-6 | 4 |
| Vu 36 | Evx91-2E-2 | 4 |
| Vu 45 | Mazagão | 4 |
| Vu 49 | BR14-Mulato | 4 |
| Vu 60 | Vila Nova | 4 |
| Vu 30 | MNC00-544D-14- | 4 |
| Vu 32 | MNC00-553D-8-1- | 4 |

TABLE 3

Sources of resistance to *Phakopsora pachyrhizi* PPUFV02 in *Vigna unguiculata* accessions from USDA-GRIN. Disease symptoms were rated using a scale ranging from 0-3 (different levels of resistance) to 4 (lack of resistance) according to lesion size and leaf area affected. Trifoliate and cotyledonary leaves were rated separately.

| | | Number of | Disease Symptoms Score | |
|---|---|---|---|---|
| Accession | PI number | plants | Cotyledonary | Trifoliate |
| Vun_00007 | 349674 | 3 | 1-2 | 0 |
| Vun_00002 | 578893 | 10 | 0-1 | 0 |
| Vun_00008 | 367918 | 12 | 0 | 0 |
| Vun_00217 | 487503 | 10 | 2-4 | 0 |
| Vun_00145 | 376864 | 9 | 0-1 | 0 |
| Vun_00218 | 487504 | 10 | 1-4 | 0 |
| Vun_00095 | 382110 | 9 | 0-1 | 0 |
| Vun_00135 | 487508 | 7 | 4 | 0 |
| Vun_011137 | 487510 | 12 | 1-4 | 0 |
| Vun_00004 | 420229 | 11 | 1-4 | 0 |
| Vun_00222 | 487433 | 11 | 1-4 | 0 |
| Vun_00139 | 527576 | 9 | 1 | 0 |
| Vun_00219 | 487507 | 9 | 1-4 | 0 |
| Vun_00136 | 487505 | 10 | 2-4 | 0 |
| Vun_00001 | 352832 | 11 | 4 | 0 |
| Van_00094 | 382109 | 10 | 0-2 | 0 |

Example 7: Identification of Germplasm as a Source of Resistance in the Genus *Lablab*

Fifty-three accessions of *Lablab purpureus* obtained from AusPGRiS with the mono-pustule isolate PPUFV02 (Table 4) were screened. Plants with two trifoliate leaves were inoculated with a suspension at $5\times10^4$ spores/ml in water amended with 0.01% Tween-80. Inoculated plants were kept for 24 h under complete darkness in a humid chamber and then transferred to the greenhouse. Symptoms were rated using a scale ranging from a (resistant) to 4 (lack of resistance) according to lesion sire and leaf area affected. Trifoliate and cotyledonary loaves were rated separately. Two accessions (IBS 059) and IBS 837) were identified that showed resistance to this fungal isolate whereas all the other accessions developed disease symptoms. The present disclosure contemplates the use of these two accessions as sources of resistance against *Phakopsora pachyrhizi*. Symptomatic accessions represent important tools in resolving individual NH-LRR genes using map-based cloning and cloned genes can provide effective field resistance as transgenes in soy.

F1 populations derived from crosses between IBS 059 and IBS 837 with several symptomatic accessions including Tamely, CPI 51565, CPI 52508, IBS 879, CPI 40167, Tamely Early, CPI 18662, RJW 35117, CPI 36903, Cor Branca and several others, were obtained in order to map and clone the corresponding resistance genes. In order to map and clone the corresponding resistance genes and based on flowering time and seed production. F2 populations derived from crosses Viçosa x IBS 837 and Tamely x IBS 059 were the focus of the next set of experiments.

Segregation analysis indicated that the resistances in these two F2 populations exhibit a 3:1 segregation toward PPUFV02, indicating that the resistance to *Phakopsora pachyrhizi* is conveyed by dominant loci. The present disclosure on templates mapping and cloning the functional genes that confer resistance at these for soy.

TABLE 4

Sources or resistance to *Phakopsora pachyrhizi* PPUFV02 in *Lablab purpureus* accessions from AusPGRIS. Disease symptoms were rated using a scale ranging from 0-3 (resistant) to 4 (lack of resistance) according to lesion size and leaf area affected. Trifoliate and cotyledonary leaves were rated separately.

| | AusTRCF | Disease Symptoms Score | |
|---|---|---|---|
| Accession | ref. No. | Cotyledonary | Trifoliate |
| CPI 29398 | 29398 | 0-4 | 0-4 |
| CPI 29399 | 29399 | 1-4 | 1-4 |
| CPI 29400 | 29400 | 1-4 | 0-4 |
| CPI 51566 | 51565 | 0-3 | 1-4 |
| IBS 867 | 52544 | 1-4 | 2-4 |
| IBS 889 | 52552 | 1-4 | 2-4 |
| DL 173 | 30213 | 1-2 | 2-3 |
| IBS 059 | 52437 | 0 | 0 |
| IBS 837 | 52518 | 0-1 | 0-1 |
| IBS 857 | 52526 | 0-4 | 0-4 |
| IBS 858 | 52527 | 0-4 | 0-4 |
| IBS 860 | 52529 | 1-4 | 3-4 |
| IBS 861 | 52530 | 2-4 | 1-3 |
| IBS 862 | 52531 | 1-4 | 0-4 |
| IBS 878 | 52519 | 1-4 | 0-3 |
| IBS 892 | 52521 | 0-4 | 0-3 |
| ILRI 13686 | 322337 | 1-4 | 1-4 |
| ILRI 13700* | | 2-4 | 2-4 |
| ILRI 14447 | 322315 | 0-4 | 1-4 |
| ILRI 14448 | 322318 | 1-4 | 3-4 |
| ILRI 11615 | 322317 | 3-4 | 1-3 |
| ILRI 14441 | 322336 | 2-4 | 1-2 |
| ILRI 11630 | 322314 | 4 | 1-4 |
| ILRI 11613 | 322334 | 4 | 1-4 |
| ILRI 10527 | 322338 | 4 | 4 |
| Cor branca | 52507 | 4 | 2-3 |
| CO 3319 | 302200 | 4 | 3-4 |
| IBS 895 | 52524 | 4 | 1-3 |
| IBS 007 | 52504 | 4 | 1-3 |
| IBS 896 | 52525 | 3-4 | 1-3 |
| RIW 5117 | 39078 | 4 | 2-3 |
| K 5116 | 28701 | 4 | 4 |
| IBS 894 | 52523 | 3-4 | 2-4 |
| IBS 859 | 52528 | 2-4 | 3 |
| IBS 879 | 52520 | 4 | 2-3 |
| IBS 569 | 52444 | 4 | 3-4 |
| CPI 51565 | 51565 | 4 | 3-4 |
| CPI 24973 | 24973 | 4 | 4 |
| Tamely early | 302199 | 4 | 3 |
| CPI 21017 | 21017 | 2-4 | 1-2 |
| ILRI 14471 | 322316 | 1-4 | 2-4 |
| ILRI 14474 | 322313 | 2-4 | 2-4 |
| ILRI 6536 | 322307 | 2-3 | 2-4 |
| ILRI 7072 | 322335 | 0-4 | 0-4 |
| M 750*** | 52510 | 1-4 | 1-4 |
| Pe pazun | 24296 | 1-4 | 0-4 |
| Tamely | 302198 | 3-4 | 3-4 |
| DBP 128 | 29803 | 3-4 | 3-4 |
| CPI 52508 | 52508 | 4 | 3-4 |
| CPI 36903 | 36903 | 4 | 3-4 |
| CPI 38705 | 38705 | 4 | 2-3 |
| CPI 40167 | 40167 | 4 | 3-4 |
| CPI 16882 | 16882 | 4 | 2-4 |

*AusTRCF ref. No. not found.

Example 8: Identification of Germplasm as a Source of Resistance in the Genus *Phaseolus*

The use of *Phaseolus vulgaris* (common bean) was tested to identify sources of resistance against *Phakopsora pachyrhizi*. *Phaseolus vulgaris* has been described as a host of *Phakopsora pachyrhizi* in field conditions (Du Preez et al, (2005) Plant Dis, 89:206; and Lynch, et al. (2006) Plant Dis., 7:970). In addition, a differential response of 16 common bean cultivars to *Phakopsora pachyrhizi*, with a cultivar-isolate interaction for severity and sporulation was reported (Miles et al. (2007) Plant Dis., 91:698-704). As a legume crop, it is unique in that it has two parallel domestication events, one in Mesoamerica and one in the Andes (Bitocchi et al. (2013) Mesoamenica and the Andes. New Phytologist 197:300-313). As a consequence, wild ancestral accessions span a large geographic area and consist of two distinct gene pools (Kwak and Gepts (2009) Theoretical and Applied Genetics 118.5:979-992). Thirteen accessions of *Phaseolus vulgaris* from Brazil (Table 5) using the same rating scale as for *Vigna unguiculata* (see. Table 3) were screened and differential responses to PPUFV02 were identified Populations from crosses between contrasting genotypes that segregate for the resistance phenotype can be generated and used for inheritance studies and genetic mapping.

The present disclosure contemplates identifying NB-LRR type resistance genes in *Phaseolus vulgaris* for efficacy in soy against *Phakopsora pachyrhizi*.

TABLE 5

Reaction of *Phaseolus vulgaris* accessions from Brazil to *Phakopsora pachyrhizi* isolate PPUFV02

| Accession | Genotype | Disease Symptoms Score |
|---|---|---|
| Pv 2 | OPNS 331 | 1 |
| Pv 9 | Vermelhinho | 1 |
| Pv 10 | Vi-4899 | 1 |
| Pv 4 | BRS Valente | 2 |
| Pv 12 | Ouro Vermelho | 2 |
| Pv 1 | BRS-MG Talismã | 4 |
| Pv 3 | Carnaval | 4 |
| Pv 5 | VC3 | 4 |
| Pv 6 | Ouro Negro | 4 |
| Pv 7 | Pérola | 4 |
| Pv 8 | Feijão vagem | 4 |
| Pv 11 | Ouro Branco | 4 |
| Pv 13 | Vermelho 2157 | 4 |

Example 9: Identification of Germplasm as a Source of Resistance in the Genus *Pisum*

A *Phakopsora pachyrhizi* screen was performed using a Brazilian single pustule isolate (PPUFV-02) on accessions from the core pea (*Pisum sativum*) collection of USDA/Grin (Table 6). Interestingly, upon inoculation of *Phakopsora pachyrhizi*, differential responses were observed in the 72 tested *Pisum sativum* accessions 21 days post-inoculation. Two accessions that were partially resistant (PI271118, and PI220189) were selected for further study. To this end, microscopy and FITC-WGA staining were carried out followed by fluorescence microscopy to monitor pathogen growth over time. These studies show that, although the pathogen is able to colonize to some extent, it is then arrested in growth.

In addition, to identifying resistant isolates, several accessions were identified that, upon visual inspection, showed lack of resistance. Two lines were evaluated in more detail (PI341888 and PI198735) showing the formation of uredinia and sporulation. Plants from resistant accessions were crossed to accessions that lacked resistance and allowed sporulation, and the resulting F1 plants were self-pollinated. F1 plants of the cross PI341888 x PI220189 and reciprocal) were used to build the first mapping population. The resulting 2 progeny (a total of 5 (plants) was screed for resistance and lack thereof and displayed a 15:1 ratio, indicating that resistance is governed by two dominant loci. Interestingly several phenotypes were observed in the F2 population a resistant phenotype (Type 0), two types of partially resistant (red-brown (RB) lesions; Type 2 and Type 3) and a clear lack of resistance (Type 4) F2 progeny. The segregation patter follows 9:3:3:1 ratio (9 resistant different RB-type resistant (partial resistance) and 1 lack of resistance). These results suggest that the two resistance loci present in this population act in a complementary fashion and both resistances are needed to convey resistance.

TABLE 6

Sources of resistance to *Phakopsora pachyrhizi* PPUFV02 in *Pisum sativum* accessions from Asia. Disease symptoms were scored as resistant (0), partially resistant (1-2) and lack of resistance with uredinia (3-4; see table legend). Two plants per accession were screened, variance in disease symptoms score indicate variation within an accession.

| Accession | Source | Disease Symptoms Score |
|---|---|---|
| Psa_00055 | PI 223527 | 0-4 |
| Psa_00056 | PI 222117 | 0 |
| Psa_00057 | PI 222071 | 1 |
| Psa_00058 | PI 220189 | 0 |
| Psa_00059 | PI 220174 | 1 |
| Psa_00060 | PI 207508 | 1 |
| Psa_00061 | PI 198735 | 4 |
| Psa_00062 | PI 134271 | 1 |
| Psa_00063 | PI 125840 | 1 |
| Psa_00064 | PI 125839 | 2 |
| Psa_00065 | PI 116944 | 1 |
| Psa_00066 | PI 429839 | 3 |
| Psa_00067 | PI 253968 | 0-4 |
| Psa_00068 | PI 210558 | 2 |
| Psa_00069 | PI 103058 | 2 |
| Psa_00070 | PI 102888 | 1-4 |
| Psa_00071 | PI 271118 | 4 |
| Psa_00072 | PI 271116 | 4 |
| Psa_00073 | PI 271115 | 0-4 |
| Psa_00074 | PI 257244 | 0-4 |
| Psa_00075 | PI 499982 | 2 |
| Psa_00070 | PI 249645 | 4 |
| Psa_00077 | PI 240516 | 3 |
| Psa_00078 | PI 212917 | 4 |
| Psa_00079 | PI 180329 | 0-4 |
| Psa_00080 | PI 179970 | 0 |
| Psa_00081 | PI 179722 | 3 |
| Psa_00082 | PI 166084 | 2 |
| Psa_00083 | PI 165949 | 1 |
| Psa_00084 | PI 164779 | 3 |
| Psa_00085 | PI 164612 | 4 |
| Psa_00086 | PI 164548 | 4 |
| Psa_00087 | PI 164182 | 2 |
| Psa_00088 | PI 163129 | 1 |
| Psa_00089 | PI 163126 | 0-3 |
| Psa_00090 | PI 121352 | 4 |
| Psa_00091 | PI 356992 | 4 |
| Psa_00092 | PI 356991 | 4 |
| Psa_00093 | PI 356986 | 4 |
| Psa_00094 | PI 356984 | 3 |
| Psa_00095 | PI 356980 | 3 |
| Psa_00096 | PI 347496 | 4 |
| Psa_00097 | PI 347490 | 4 |
| Psa_00098 | PI 347477 | 4 |
| Psa_00099 | PI 347457 | 0-4 |
| Psa_00100 | PI 347295 | 4 |
| Psa_00101 | PI 347281 | 3 |
| Psa_00102 | PI 308796 | 3 |
| Psa_00103 | PI 356974 | 4 |
| Psa_00104 | PI 356973 | 2 |
| Psa_00105 | PI 271511 | 4 |
| Psa_00106 | PI 639967 | 4 |
| Psa_00107 | PI 173840 | 2-4 |
| Psa_00108 | PI 221697 | 4 |
| Psa_00109 | PI 212031 | 4 |
| Psa_00110 | PI 143485 | 2 |
| Psa_00111 | PI 140298 | 4 |
| Psa_00112 | PI 227258 | 4 |
| Psa_00113 | PI 174921 | 0-4 |
| Psa_00114 | PI 286431 | 4 |

TABLE 6-continued

Sources of resistance to *Phakopsora pachyrhizi* PPUFV02 in *Pisum sativum* accessions from Asia. Disease symptoms were scored as resistant (0), partially resistant (1-2) and lack of resistance with uredinia (3-4; see table legend). Two plants per accession were screened, variance in disease symptoms score indicate variation within an accession.

| Accession | Source | Disease Symptoms Score |
| --- | --- | --- |
| Psa__00115 | PI 286430 | 0-4 |
| Psa__00116 | PI 271038 | 4 |
| Psa__00117 | PI 124478 | 4 |
| Psa__00118 | PI 274308 | 4 |
| Psa__00119 | PI 274307 | 1 |
| Psa__00120 | PI 269543 | 4 |
| Psa__00121 | PI 116844 | 4 |
| Psa__00122 | PI 241593 | 1-3 |
| Psa__00123 | PI 286607 | 0-4 |
| Psa__00124 | PI 156720 | 4 |
| Psa__00125 | PI 355906 | 4 |
| Psa__00126 | PI 378157 | 4 |

*Disease score. In which 0 = Resistant; absence macroscopic and microscopic symptoms. 1 = Partial Resistance; small ≤250 µm patches of reddish-brown necrosis caused by mycelial growth visible using FITC-Wheat germ agglutinin (WGA) stain followed by fluorescence microscopy. 2 = Partial Resistance; infection patches of ≤1000 µm reddish-brown necrosis caused by mycelial growth visible using FITC-WGA stain followed by fluorescence microscopy. 3 = Lack of Resistance; clear infection structures and/or uredinia, mycelium visible using bright-livid microscopy, no sporulation. 4 = Lack of Resistance; lesions with or without necrosis, with the presence of fully formed uredinia and sporulation.

Example 10: Testing of CcRpp1 Transgenics with Additional *Phakopsora pachyrhizi* Isolates In order to assess the effectiveness of CcRpp1 against additional, current U.S. field isolates, homozygous and null plantlets of Event 71 were independently inoculated with 20,000 sp/ml of the GA15 (Georgia) and AR15 (Arkansas) isolates. These *Phakopsora* isolates were obtained from infected leaves harvested from soybean fields in Decatur, Ga. and Mound Bayou, AR, respectively. Inoculations and incubations were done as previously described, except that fresh spores were collected from a susceptible variety, and therefore, no heat-shock was necessary scoring took place 15 days after inoculation. The experiments rendered high severity on the null and susceptible control plants, with numerous tan lesions, while homozygous plants showed immunity to both isolates, as summarized in Table 7. Sample sizes, however, were too small for statistical analyses.

TABLE 7

Measured traits for CcRppl inoculations with two field isolates. Zygosity is used as transgene copy number (null = 0, hemiz = 1, homoz = 2); R = resistant, R = partial resistance S = susceptible; Avg LC/cm$^2$ = average lesion count per area unit (cm$^2$).

| Isolate | Zygosity | n | Reaction | Lesion type | Avg(LC/cm$^2$) |
|---|---|---|---|---|---|
| AR15 | Homoz | 20 | R | Resistant | 0.01 |
| | Hemiz | 5 | PR | RB | 0.09 |
| | Null | 5 | S | Tan | 7.93 |
| | Susceptible Control | 13 | S | Tan | 12.63 |
| GA15 | Homoz | 21 | R | Resistant | 0.001 |
| | Hemiz | 8 | PR | RB | 0.08 |
| | Null | 2 | S | Tan | 19.44 |
| | Susceptible Control | 12 | S | Tan | 23.22 |

These data demonstrate that transgenic plants carrying CcRpp1 in the homozygous state are resistant and hemizygous plants show partial resistance to at least three field isolates of *Phakopsora pachyrhizi*.

Example 11: Transformation of Soybean with the CcRpp1 Construct PHP74119

Isolation of CcRpp1 transgenic events was achieved via biolistic delivery of DNA as disclosed in Example 3. Insertion of the transgene and marker DNA into the soy genome was then achieved by a targeted integration approach. This site specific integration (SSI) procedure relies on the FLP/FRT recombination system, is well known to those skilled in the art of plant transformation and is described in La et al. (2009) Plant Physiol. 151: 1087. The transgenic events of Example 3 were generated by bombardment of DNA into the 93B86-5.1 transformation line. Additional SSI events were obtained by delivery of DNA into the 93B86-TB line that differs from the former line with respect to chromosomal location of the integration site. For this experiment, a new CcRpp1 transformation construct (PHP74119) was assembled via ligation of the 2791 bp CcRpp1 coding region to a 1959 bp fragment containing the soybean ubiquitin promoter+Intron I and a 880 bp *Arabidopsis* ubiquitin terminator fragment.

Biolistic transformation of soybean line 93B6-T5. Transgenic soybean lines were obtained by delivery of DNA (PHP74119 and a FLP recombinase construct) into embryogenic suspension callus cultures (93B86-TB5) using particle bombardment (U.S. Pat. No. 4,945,050) with a BIORAD Biolistic PDS1000/He instrument. Site-specific integration of the GmUbi-CcRpp1 gene into the soybean genome was achieved by recombinase mediated cassette exchange (RMCE) as described in Li et al, 2009. Transgenic events were identified following selection on 100 ppb chlorsulfuron and somatic embryos regenerated to produce T0 plantlets that were advanced for T1 seed production. Identification and characterization of RMCE events was performed using qPCR, as described in Li et al, 2009.

Testing of PH74119 transgenic events in 93B86-TB5s. From 2 transformation experiments (Soy 5342 and Soy 5861), a total of 3 transgenic events were recovered that were found by qPCR to contain high quality, single copy insertions of the CcRpp1 transgene. All three events were advanced for T1 testing against ASR, using the methods described in Example 4.

T1 seeds from the three events were planted, sampled and inoculated as described in Example 4; plants were scored 15 days after inoculation. The effect of CcRpp was observed and confirmed in plants from two events (Soy 5342.11.1 and Soy 5342.11.2). Hemizygous plants showed partial resistance with reduced amount of RB lesions while homozygous plants were resistant. In this case, the construct's effect on reduction of severity in the hemizygous plants was approximately 98%, a more pronounced effect than previously detected in the 5.1 background. Results from the confirmation experiment are summarized in Table. The third event (Soy 5861.1.1), however, did not show a difference in disease severity between transgenic and null plants. In order to identify the differences between the effective and non-effective events, transcript amount was assessed through qRT-PCR for all three events. The results showed higher expression m the two effective events, while event Soy 5861.1.1 displayed lower expression of the CcRpp1 transcript.

TABLE 8

Measured traits for two transformation events of GmUbi-CcRppl in TB5 background. Zygosity is used as transgene copy number (null = 0, hemiz = 1, homoz = 2)
R = resistant, PR = partial resistance, S = susceptible;
Avg LC/$cm^2$ = average lesion count per area unit ($cm^2$).

| Event | Zygosity | n | Reaction | Lesion type | Avg(LC/$cm^2$) |
|---|---|---|---|---|---|
| Soy | Homoz | 14 | R | Resistant | 0 |
| 5342.11.1 | Hemiz | 40 | PR | RB | 0.25 |
| | Null | 25 | S | Tan | 6.64 |
| Soy | Homoz | 15 | R | Resistant | 0 |
| 5342.11.2 | Hemiz | 43 | PR | RB | 0.52 |
| | Null | 20 | S | Tan | 5.94 |

These results confirm the efficacy of the CcRpp1 gene against *Phakopsora pachyrhizi*. GA05. In these experiments, a second overexpression CcRpp1 construct (PHP74119) was independently generated and introduced into an additional soybean line (93B86-TB5) and high quality transformation events were isolated and tested. The ASR infection assays provide further validation of the CcRpp1 gene with resistance found in homozygotes, and strong but partial resistance observed in hemizygotes.

The sequences referred to herein, SEQ. 10 NOs: 1-8 are filed concurrently herewith in a textfile and are incorporated herein in their entireties.

As used herein the singular forms "a", "and", and "the" include plural referents unless the context clearly dictates otherwise. Thus, for example, reference to "a cell" includes a plurality of such cells and reference to "the protein" includes reference to one or more proteins and equivalents thereof known to those skilled in the art, and so forth. All technical and scientific terms used herein have the same meaning as commonly understood to one of ordinary skill in the art to which this invention belongs unless clearly indicated otherwise.

As used in the specification and in the claims, the term "comprising" can include the aspects "consisting of" and "consisting essentially of." "Comprising can also mean "including but not limited to."

The word "or" as used herein means any one member of a particular list and also includes any combination of members of that list.

The term "soybean" as used herein refers to *Glycine max* and any plant variety bred or cultivated with soybean.

Ranges can be expressed herein as from "about" one particular value, and/or to "about" another particular value. When such a range is expressed, a further aspect includes from the one particular value and/or to the other particular value. Similarly, when values are expressed as approximations, by use of the antecedent "about," it will be understood that the particular value forms a further aspect. It will be further understood that the endpoints of each of the ranges are significant both in relation to the other endpoint and independently of the other endpoint. It is also understood that there are a number of values disclosed herein and that each value is also herein disclosed as "about" that particular value in addition to the value itself. For example, if the value "10" is disclosed, then "about 10" is also disclosed. It is also understood that each unit between two particular units is also disclosed. For example, if 10 and 15 are disclosed, then 11, 12, 13, and 14 are also disclosed.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

What is claimed is:

1. A recombinant DNA construct comprising a heterologous regulatory element operably linked to a polynucleotide comprising a nucleotide sequence encoding a legume-derived nucleotide binding site-leucine-rich repeat (NB-LRR) polypeptide having at least 90% amino acid sequence identity to SEQ ID NO: 2.

2. A method of conferring disease resistance in a legume crop species, the method comprising transforming a legume crop species with a polynucleotide comprising a nucleotide sequence encoding a legume-derived nucleotide-binding site-leucine-rich repeat (NB-LRR) polypeptide having at least 90% amino acid sequence identify to SEQ ID NO: 2 that confers disease resistance to a legume crop species disease.

3. The method of claim 2, wherein the legume crop species disease is caused by a plant pathogen.

4. The method of claim 3, wherein the plant pathogen is *Phakopsora pachyrhizi* or *Phakopsora meibomiae*.

5. The method of claim 2, wherein the legume crop species disease is Asian soybean rust.

6. The method of claim 2, wherein the legume crop species is an alfalfa, clover, pea, bean lentil, lupin, mesquite, carob, soybean, peanut or tamarind.

7. The method of claim 2, wherein the legume crop species is soybean.

8. A method of enhancing plant resistance to Asian soybean rust (ASR) disease, the method comprising conferring resistance to an ASR pathogen by introgression of a polynucleotide comprising a nucleotide sequence encoding a legume-derived nucleotide-binding site-leucine-rich repeat (NB-LRR) polypeptide having at least 90% amino acid sequence identify to SEQ ID NO: 2 into germplasm in a breeding program for resistance to ASR.

9. The method of claim 8, where in the germplasm is an alfalfa, clover, pea, bean, lentil, lupin, mesquite, carob, soybean, peanut or tamarind species.

10. The method of claim 8, wherein the ASR is caused by *Phakopsora pachyrhizi* or *Phakopsora meibomiae*.

11. The recombinant DNA construct of claim 1, further comprising one or more resistance genes.

12. The recombinant DNA construct of claim 11, further comprising one or more polynucleotide sequences of interest.

* * * * *

SEQUENCE LISTING

```
<160> NUMBER OF SEQ ID NOS: 8

<210> SEQ ID NO 1
<211> LENGTH: 2778
<212> TYPE: DNA
<213> ORGANISM: Cajanus cajan

<400> SEQUENCE: 1
atggcagaca gtgtggtttc ctttgtttta gatcacttgt cccaactggt ggaacatgaa     60
gcaaggttgc taagtggcgt ggaagacaag gtgaagtccc tcgagaggga gcttcagatg    120
atcaacgtca tcctaagaac cacaaacagc aacaacgaca ttcagaaaac agtggtgagc    180
caaatcagag atgtggccca tgaagctgag gatgtcattg acacgtacgt tgccaaagtg    240
gccctgcaca acaggagaac catgctgggg aggctactcc atggagttga ccaaacaaag    300
ttgctccatg acgtatccga gaaaatagac gagatcataa caactctcaa ccagatacgt    360
gaaaacaaga tcaaatacag cgagttccaa gaaagaaatc atcaatccat agcagaagag    420
gaggaggagg agaaggagag ggagaggtta cttcacaagc taagaagaaa tgtagaggag    480
gaacatgtag tgggttttat ccgtggatct caagcaatca tcaagctact caaggaaggt    540
ggctcacggc gtaatgtggt ctccatcatc ggcatggggg ggttgggcaa gaccaccctt    600
gcccgaaaag tttataatga tagcaaggtg aaacaaggct ttagttgttg tgtttgggtg    660
```

```
tacgtgtcaa acgagtgtag agctaaggag cttttgctta gtcttcttaa gcatttgagg    720
ccaaacctcg aaactgaact tcaagaagaa acaacaaag gaaaaaatt cactgaagaa      780 caagacattt ttaacttgag tgtggaggag ctgaagaaac tggtgcggca atacttggag    840
aggaaaacaa ggtatctggt ggtcctcgat gacttgtgga aaacacaaga ttgggacgag    900
gtgcaagatg cttttcccga caacaacaga ggcaacagaa tattgatcac tagtcgtttg    960
aaagaggtgg ccttgcatac tagtcttcat cctccatact accttcaatt tctcagccaa   1020
gaagaaagct gggagctctt tcgtaggaaa gtgtttagag gggaagaatg ccctttttgaa  1080 ctagagcctc taggcaaaca aatagtggca agttgtcgcg gtttgccact ctctattgtt   1140
gtattagcag gattgctagc caacaaggaa aagtcacaca gggaatggtc caaagtggtg   1200
ggtcacgtca actggtatct tactcaagac gagactcaag tgaaggatat agttctgaag   1260
ctcagttatg ataacttgcc aagaagattg aaaccatgct ttctatattt tgggatattc   1320
cctgaagact ttgaaatccc tgttaggcca ttactacaac aatgggttgc agaagggttt   1380
atacaagaaa caagaaatag agacccagat gatgtggcag aagactactt gtacgagctc   1440
attgatcgta gtttggtcca agtagcagca ataaagacta gtggaggtgt gaaaacttgt   1500
cacatccatg atcttctccg agatctttgt gtatcgcaga gcaaagggga caagattttt   1560
gaagtctgct cagataatga cattcaaatt ctaacaaaac ctcgcaggtt gtccttccat   1620
tgtgacatgg gccactacat ttcttcaagc aacaaagacc attcatgtat ccgttctttg   1680
ttcttctttg gaatatattc caattttact gggaacgagt gggaatggct tttcaaaggc   1740
ttcaaattgg ttcgagtgtt agagcttgga aaaaaccatt gcgcaggaaa gatcccatct   1800
aatttggggg actttatcca cttaaggtat ttgagaattg actcgaattt tggtataatt   1860
attccaactt ccatacttac ccttcagaat ttacaaacag tagatttagg taattggttt   1920
agggaaatcc caatttgttt ccctgctcaa atgtggaagc tcaaacattt aaggcacctg   1980
tatgggcaag gacctgtgaa gcttcaaggc cactattcag gatcaaatga ggttatgtgg   2040
aatctccgaa ccatcttccc cattgatatt gatacacaaa cattgtctct gatgaagaaa   2100
ggaagcttcc ccaatcttgt gaaattgggg ttgtcaatca attcggaccg ccaaggtaag   2160
tggccaaagt tgttgcagag cttacaagaa ttaagtcatt tgaatatctt aaagatttgc   2220
ctccgagggg attttgatgc ttcaataggc acagtgtcaa gcatatgcg gtttggttgt    2280 gagccacagg agctattaca aagcctaggg ttgttgactc atataactac gttgaaaatc   2340
accaatatct gcagccttat gataacggtt cctccaaatg tcaccaagtt aacattgcgt   2400
ggtattagta gcatcactag ggaggggctg aatgcgttga gaaatcacac caaactccaa   2460
attttgagtc tatatggaga ctatggctct aacattaacc tcaattgtgt tgtaggcggc   2520
tttccacaac tgcaagtatt gcaattgaaa aagttcacct ctgtaaattg gaaattaggc   2580
aatggtgcaa tgccacgtct tcacactcta gtcatcatca actgtcaaag tttagatgat   2640
cttccaaatg aattgtggtc tctcactgcc ttcagaaaac tgcatgtaaa acaaccctca   2700
caaccaatgc ttcgtatgct acgggatttg aaaataaagg atagggttca agtcatagtc   2760
gatgatcatg acaactag                                                 2778
```

<210> SEQ ID NO 2
<211> LENGTH: 925
<212> TYPE: PRT
<213> ORGANISM: Cajanus cajan

```
<400> SEQUENCE: 2

Met Ala Asp Ser Val Val Ser Phe Val Leu Asp His Leu Ser Gln Leu
1               5                   10                  15

Val Glu His Glu Ala Arg Leu Leu Ser Gly Val Glu Asp Lys Val Lys
            20                  25                  30

Ser Leu Glu Arg Glu Leu Gln Met Ile Asn Val Ile Leu Arg Thr Thr
        35                  40                  45

Asn Ser Asn Asn Asp Ile Gln Lys Thr Val Val Ser Gln Ile Arg Asp
    50                  55                  60

Val Ala His Glu Ala Glu Asp Val Ile Asp Thr Tyr Val Ala Lys Val
65                  70                  75                  80

Ala Leu His Asn Arg Arg Thr Met Leu Gly Arg Leu Leu His Gly Val
                85                  90                  95

Asp Gln Thr Lys Leu Leu His Asp Val Ser Glu Lys Ile Asp Glu Ile
            100                 105                 110

Ile Thr Thr Leu Asn Gln Ile Arg Glu Asn Lys Ile Lys Tyr Ser Glu
        115                 120                 125

Phe Gln Glu Arg Asn His Gln Ser Ile Ala Glu Glu Glu Glu Glu Glu
    130                 135                 140

Lys Glu Arg Glu Arg Leu Leu His Lys Leu Arg Arg Asn Val Glu Glu
145                 150                 155                 160

Glu His Val Val Gly Phe Ile Arg Gly Ser Gln Ala Ile Ile Lys Leu
                165                 170                 175

Leu Lys Glu Gly Gly Ser Arg Arg Asn Val Val Ser Ile Ile Gly Met
            180                 185                 190

Gly Gly Leu Gly Lys Thr Thr Leu Ala Arg Lys Val Tyr Asn Asp Ser
        195                 200                 205

Lys Val Lys Gln Gly Phe Ser Cys Cys Val Trp Val Tyr Val Ser Asn
    210                 215                 220

Glu Cys Arg Ala Lys Glu Leu Leu Ser Leu Leu Lys His Leu Arg
225                 230                 235                 240

Pro Asn Leu Glu Thr Glu Leu Gln Glu Glu Asn Asn Lys Gly Lys Lys
                245                 250                 255

Phe Thr Glu Glu Gln Asp Ile Phe Asn Leu Ser Val Glu Glu Leu Lys
            260                 265                 270

Lys Leu Val Arg Gln Tyr Leu Glu Arg Lys Thr Arg Tyr Leu Val Val
        275                 280                 285

Leu Asp Asp Leu Trp Lys Thr Gln Asp Trp Asp Glu Val Gln Asp Ala
    290                 295                 300

Phe Pro Asp Asn Asn Arg Gly Asn Arg Ile Leu Ile Thr Ser Arg Leu
305                 310                 315                 320

Lys Glu Val Ala Leu His Thr Ser Leu His Pro Pro Tyr Tyr Leu Gln
                325                 330                 335

Phe Leu Ser Gln Glu Glu Ser Trp Glu Leu Phe Arg Arg Lys Val Phe
            340                 345                 350

Arg Gly Glu Glu Cys Pro Phe Glu Leu Glu Pro Leu Gly Lys Gln Ile
        355                 360                 365

Val Ala Ser Cys Arg Gly Leu Pro Leu Ser Ile Val Val Leu Ala Gly
    370                 375                 380

Leu Leu Ala Asn Lys Glu Lys Ser His Arg Glu Trp Ser Lys Val Val
385                 390                 395                 400

Gly His Val Asn Trp Tyr Leu Thr Gln Asp Glu Thr Gln Val Lys Asp
                405                 410                 415
```

```
Ile Val Leu Lys Leu Ser Tyr Asp Asn Leu Pro Arg Leu Lys Pro
            420                 425                 430

Cys Phe Leu Tyr Phe Gly Ile Phe Pro Glu Asp Phe Glu Ile Pro Val
            435                 440                 445

Arg Pro Leu Leu Gln Gln Trp Val Ala Glu Gly Phe Ile Gln Glu Thr
            450                 455                 460

Arg Asn Arg Asp Pro Asp Val Ala Glu Asp Tyr Leu Tyr Glu Leu
465             470                 475                 480

Ile Asp Arg Ser Leu Val Gln Val Ala Ala Ile Lys Thr Ser Gly Gly
            485                 490                 495

Val Lys Thr Cys His Ile His Asp Leu Leu Arg Asp Leu Cys Val Ser
            500                 505                 510

Gln Ser Lys Gly Asp Lys Ile Phe Glu Val Cys Ser Asp Asn Asp Ile
            515                 520                 525

Gln Ile Leu Thr Lys Pro Arg Arg Leu Ser Phe His Cys Asp Met Gly
            530                 535                 540

His Tyr Ile Ser Ser Ser Asn Lys Asp His Ser Cys Ile Arg Ser Leu
545                 550                 555                 560

Phe Phe Phe Gly Ile Tyr Ser Asn Phe Thr Gly Asn Glu Trp Glu Trp
            565                 570                 575

Leu Phe Lys Gly Phe Lys Leu Val Arg Val Leu Glu Leu Gly Lys Asn
            580                 585                 590

His Cys Ala Gly Lys Ile Pro Ser Asn Leu Gly Asp Phe Ile His Leu
            595                 600                 605

Arg Tyr Leu Arg Ile Asp Ser Asn Phe Gly Ile Ile Pro Thr Ser
            610                 615                 620

Ile Leu Thr Leu Gln Asn Leu Gln Thr Val Asp Leu Gly Asn Trp Phe
625                 630                 635                 640

Arg Glu Ile Pro Ile Cys Phe Pro Ala Gln Met Trp Lys Leu Lys His
                    645                 650                 655

Leu Arg His Leu Tyr Gly Gln Gly Pro Val Lys Leu Gln Gly His Tyr
            660                 665                 670

Ser Gly Ser Asn Glu Val Met Trp Asn Leu Arg Thr Ile Phe Pro Ile
            675                 680                 685

Asp Ile Asp Thr Gln Thr Leu Ser Leu Met Lys Lys Gly Ser Phe Pro
            690                 695                 700

Asn Leu Val Lys Leu Gly Leu Ser Ile Asn Ser Asp Arg Gln Gly Lys
705                 710                 715                 720

Trp Pro Lys Leu Leu Gln Ser Leu Gln Glu Leu Ser His Leu Asn Ile
            725                 730                 735

Leu Lys Ile Cys Leu Arg Gly Asp Phe Asp Ala Ser Ile Gly Thr Val
            740                 745                 750

Ser Ser Ile Trp Arg Phe Gly Cys Glu Pro Gln Glu Leu Leu Gln Ser
            755                 760                 765

Leu Gly Leu Leu Thr His Ile Thr Thr Leu Lys Ile Thr Asn Ile Cys
            770                 775                 780

Ser Leu Met Ile Thr Val Pro Pro Asn Val Thr Lys Leu Thr Leu Arg
785                 790                 795                 800

Gly Ile Ser Ser Ile Thr Arg Glu Gly Leu Asn Ala Leu Arg Asn His
                    805                 810                 815

Thr Lys Leu Gln Ile Leu Ser Leu Tyr Gly Asp Tyr Gly Ser Asn Ile
            820                 825                 830
```

```
Asn Leu Asn Cys Val Val Gly Gly Phe Pro Gln Leu Gln Val Leu Gln
            835                 840                 845

Leu Lys Lys Phe Thr Ser Val Asn Trp Lys Leu Gly Asn Gly Ala Met
    850                 855                 860

Pro Arg Leu His Thr Leu Val Ile Ile Asn Cys Gln Ser Leu Asp Asp
865                 870                 875                 880

Leu Pro Asn Glu Leu Trp Ser Leu Thr Ala Phe Arg Lys Leu His Val
                885                 890                 895

Lys Gln Pro Ser Gln Pro Met Leu Arg Met Leu Arg Asp Leu Lys Ile
            900                 905                 910

Lys Asp Arg Val Gln Val Ile Val Asp Asp His Asp Asn
            915                 920                 925

<210> SEQ ID NO 3
<211> LENGTH: 2862
<212> TYPE: DNA
<213> ORGANISM: Glycine max

<400> SEQUENCE: 3
```

| | | | | | |
|---|---|---|---|---|---|
| atggcggaca | gtgtggtttc | ctttgtatta | gatcacttgt | ctcaactgat | ggcacgtgaa | 60 |
| gcaaagttgc | tgtgtggcgt | ggaagacagg | atcaagtccc | tccaaaatga | gcttgaaatg | 120 |
| atcaatgagt | tcctcaatac | ctcaaagagc | aaaaagggga | ttgagaaaaa | agtggtgagc | 180 |
| caaatcagag | atgttgccca | tctagctgag | gatgtcatcg | acacatacgt | tgccaaagtt | 240 |
| gccatacacg | agaggagaac | catgatgggt | aggctcctcc | atagcgttca | ccaagcacgg | 300 |
| ttgctccatg | acgtagctga | gaaaatagac | cagataaaaa | acactgtcag | tgagatacgc | 360 |
| aacaacaaga | tcaaatatga | agaattccaa | gaaagcaaca | atcaatccac | aacaaaagca | 420 |
| gaggaggagg | agaaggaaag | ggcgcaatta | ctacacaaga | taagaagaaa | tgtggaggaa | 480 |
| gaagatgtag | taggctttgt | acgtgactcc | aacgtagtca | tcaagcgact | cctagaaggt | 540 |
| ggttcatctc | gtaacgttgt | ctccatcatt | ggcatgggtg | gattgggcaa | gaccaccctt | 600 |
| gccccgaaagg | tctataacag | cagagaggtg | aaacaatact | ttagatgttg | cgcgtgggtt | 660 |
| tatgtgtcaa | acgagtgtag | agtcaaggag | atttttcttg | gccttcttaa | gcatttgatg | 720 |
| ccaagccttg | aataccaatg | tagaggcaac | aagaaaggta | gaaacacac | aagagaatta | 780 |
| aacatttcta | aattaaacga | ggaggagttg | aagaaactgg | tgagagaatg | cttggagagg | 840 |
| aaaaggtatc | tggtggtcct | cgatgacctg | tggaaaacac | aagattggga | cgagttgcac | 900 |
| gatgcttttc | ctgacgacaa | caaaggcagc | aggatattga | ttactagtcg | tttgaaagag | 960 |
| gtggcgttgc | atactagcca | tcatcctcct | tactatcttc | agtttcttag | tgaagatgaa | 1020 |
| agtgggagc | tcttctgcaa | gaaagtgttt | aggggcgaag | agtactcttc | tgatttggag | 1080 |
| cctttgggga | aacagatagt | tcaaagttgt | cgtggtttgc | cactctcaat | cgtggtgtta | 1140 |
| gcagggttgc | tagccaacaa | ggaaaaatca | tatagagaat | ggtctaaagt | ggtgggtcat | 1200 |
| gtcaactggt | atcttactca | agatgagacc | caagtgaagg | atatagttct | caaactcagc | 1260 |
| tatgacaacc | tgccaaggag | attgaaacca | tgctttctgt | tcttgggat | attccccgaa | 1320 |
| gactttgaaa | tccagttag | gccattattg | caacgatggg | ttgccgaagg | atttatacaa | 1380 |
| gaaacaggga | atagagaccc | agatgatgtt | gctgaagact | acttgtacga | gctcattgat | 1440 |
| cgtagtttgg | tccaagtagc | agctatgaag | actagtggag | gtgtgaagac | ttgtcacatc | 1500 |
| catgatcttc | ttcgagatct | ttgcatatca | gagagcaaag | aggacaaggt | tttccaagtt | 1560 |
| tgcacaggta | ataacattct | aatctccaca | aaaccccgca | gactgtccat | tcattgtaac | 1620 |

```
atgggtgatt acatttcttc aaataacaat gaccagtcat gtattcgttc tttgttcatg    1680
tttggacccc attattttt tatcccaagc gagttgaaaa acttttcaa aggcttcaaa     1740 ttggttcgag tgttagagct tggaacagac agttgtggag aaagattcc atctaatttg    1800 ggggacttta tccacttaag gtatttgaga attgactcgc aacatgttag aattattcca   1860
gattctatac ttacccttca gaatttacaa accgtagacc taggttgttg cgtttgact    1920 attccaattt ctttccctgc tcaaatatgg aagctcaaac attttaaggca tttgtatgcg  1980 ccagggccta tcaagcttag aggccacaat tcaaaaccaa gtgaggttat gtggaatctt   2040
caaaccatga acgccattgt gttggacgaa caaacatcat atttgataaa taaaggaact   2100
ttccccaacc ttaagaattt aagtctgcaa atatcttcgg gtcgcaaggc taaatggcct   2160
aagttgttgc agagcctaca acaattaagt catttgagta agttaaggat ttccttgaa    2220 atcaattttt gtgaaggttc actgtccgga aactatatga aaagcatgga gtggcacatt   2280
ggttgtaagc cgcaagaagt attacaatgc ataggggcagt tgagtcatgt aactacgctg  2340
aaaattgtca atgccttgga ccttctaaca tgtagggtca cgtttcctcc aaatgttata   2400
aagttaacat tgacaggtat tagttgtgtg actgatgagg gaatggattc tttgggaaat   2460
cacacgaaac tccaaaaatt gagactaact agaggaattt tgtcagaatc ctttgacctc   2520
aattgtgttg caggaaggtt cccacaactg caggtgtttg agatgagtgg tttgaaagtt   2580
agaaactgga aattaggcaa cagtgcaatg ttatgcctcc aaagtctgat catccacaaa   2640
tgtaaaatgt tagatggcat cccaaatgaa ctgtggtctt tgattgcttt gagaaaagtg   2700
caagtaaagc aaccctcaga agcaatggct cgcatgctac aaaacttgga aatgaaggat   2760
ggggttgaac ttatagttga accgaaggaa cgtcatgatt ctactgtaat attatctatg   2820
gatgaaattt gggaggcatt taattcacgt ggtatttgtt ag                      2862
```

<210> SEQ ID NO 4
<211> LENGTH: 953
<212> TYPE: PRT
<213> ORGANISM: Glycine max

<400> SEQUENCE: 4

```
Met Ala Asp Ser Val Val Ser Phe Val Leu Asp His Leu Ser Gln Leu
1               5                   10                  15

Met Ala Arg Glu Ala Lys Leu Leu Cys Gly Val Glu Asp Arg Ile Lys
            20                  25                  30

Ser Leu Gln Asn Glu Leu Glu Met Ile Asn Glu Phe Leu Asn Thr Ser
        35                  40                  45

Lys Ser Lys Lys Gly Ile Glu Lys Lys Val Val Ser Gln Ile Arg Asp
    50                  55                  60

Val Ala His Leu Ala Glu Asp Val Ile Asp Thr Tyr Val Ala Lys Val
65                  70                  75                  80

Ala Ile His Glu Arg Arg Thr Met Met Gly Arg Leu Leu His Ser Val
                85                  90                  95

His Gln Ala Arg Leu Leu His Asp Val Ala Glu Lys Ile Asp Gln Ile
            100                 105                 110

Lys Asn Thr Val Ser Glu Ile Arg Asn Asn Lys Ile Lys Tyr Glu Glu
        115                 120                 125

Phe Gln Glu Ser Asn Asn Gln Ser Thr Thr Lys Ala Glu Glu Glu Glu
    130                 135                 140

Lys Glu Arg Ala Gln Leu Leu His Lys Ile Arg Arg Asn Val Glu Glu
```

-continued

```
            145                 150                 155                 160
Glu Asp Val Val Gly Phe Val Arg Asp Ser Asn Val Val Ile Lys Arg
                    165                 170                 175

Leu Leu Glu Gly Gly Ser Ser Arg Asn Val Ser Ile Ile Gly Met
                180                 185                 190

Gly Gly Leu Gly Lys Thr Thr Leu Ala Arg Lys Val Tyr Asn Ser Arg
                195                 200                 205

Glu Val Lys Gln Tyr Phe Arg Cys Cys Ala Trp Val Tyr Val Ser Asn
    210                 215                 220

Glu Cys Arg Val Lys Glu Ile Phe Leu Gly Leu Leu Lys His Leu Met
225                 230                 235                 240

Pro Ser Leu Glu Tyr Gln Cys Arg Gly Asn Lys Lys Gly Lys Lys His
                245                 250                 255

Thr Arg Glu Leu Asn Ile Ser Lys Leu Asn Glu Glu Leu Lys Lys
            260                 265                 270

Leu Val Arg Glu Cys Leu Glu Arg Lys Arg Tyr Leu Val Val Leu Asp
                275                 280                 285

Asp Leu Trp Lys Thr Gln Asp Trp Asp Glu Leu His Asp Ala Phe Pro
    290                 295                 300

Asp Asn Lys Gly Ser Arg Ile Leu Ile Thr Ser Arg Leu Lys Glu
305                 310                 315                 320

Val Ala Leu His Thr Ser His His Pro Pro Tyr Tyr Leu Gln Phe Leu
                325                 330                 335

Ser Glu Asp Glu Ser Trp Glu Leu Phe Cys Lys Lys Val Phe Arg Gly
                340                 345                 350

Glu Glu Tyr Ser Ser Asp Leu Glu Pro Leu Gly Lys Gln Ile Val Gln
            355                 360                 365

Ser Cys Arg Gly Leu Pro Leu Ser Ile Val Val Leu Ala Gly Leu Leu
    370                 375                 380

Ala Asn Lys Glu Lys Ser Tyr Arg Glu Trp Ser Lys Val Val Gly His
385                 390                 395                 400

Val Asn Trp Tyr Leu Thr Gln Asp Glu Thr Gln Val Lys Asp Ile Val
                405                 410                 415

Leu Lys Leu Ser Tyr Asp Asn Leu Pro Arg Arg Leu Lys Pro Cys Phe
                420                 425                 430

Leu Phe Leu Gly Ile Phe Pro Glu Asp Phe Glu Ile Pro Val Arg Pro
            435                 440                 445

Leu Leu Gln Arg Trp Val Ala Glu Gly Phe Ile Gln Glu Thr Gly Asn
    450                 455                 460

Arg Asp Pro Asp Asp Val Ala Glu Asp Tyr Leu Tyr Glu Leu Ile Asp
465                 470                 475                 480

Arg Ser Leu Val Gln Val Ala Ala Met Lys Thr Ser Gly Gly Val Lys
                485                 490                 495

Thr Cys His Ile His Asp Leu Leu Arg Asp Leu Cys Ile Ser Glu Ser
                500                 505                 510

Lys Glu Asp Lys Val Phe Gln Val Cys Thr Gly Asn Asn Ile Leu Ile
            515                 520                 525

Ser Thr Lys Pro Arg Arg Leu Ser Ile His Cys Asn Met Gly Asp Tyr
    530                 535                 540

Ile Ser Ser Asn Asn Asp Gln Ser Cys Ile Arg Ser Leu Phe Met
545                 550                 555                 560

Phe Gly Pro His Tyr Phe Ile Pro Ser Glu Leu Lys Arg Leu Phe
                565                 570                 575
```

-continued

Lys Gly Phe Lys Leu Val Arg Val Leu Glu Leu Gly Thr Asp Ser Cys
            580                 585                 590

Gly Gly Lys Ile Pro Ser Asn Leu Gly Asp Phe Ile His Leu Arg Tyr
        595                 600                 605

Leu Arg Ile Asp Ser Gln His Val Arg Ile Ile Pro Asp Ser Ile Leu
    610                 615                 620

Thr Leu Gln Asn Leu Gln Thr Val Asp Leu Gly Cys Trp Arg Leu Thr
625                 630                 635                 640

Ile Pro Ile Ser Phe Pro Ala Gln Ile Trp Lys Leu Lys His Leu Arg
                645                 650                 655

His Leu Tyr Ala Pro Gly Pro Ile Lys Leu Arg Gly His Asn Ser Lys
            660                 665                 670

Pro Ser Glu Val Met Trp Asn Leu Gln Thr Met Asn Ala Ile Val Leu
        675                 680                 685

Asp Glu Gln Thr Ser Tyr Leu Ile Asn Lys Gly Thr Phe Pro Asn Leu
    690                 695                 700

Lys Asn Leu Ser Leu Gln Ile Ser Ser Gly Arg Lys Ala Lys Trp Pro
705                 710                 715                 720

Lys Leu Leu Gln Ser Leu Gln Gln Leu Ser His Leu Ser Lys Leu Arg
                725                 730                 735

Ile Ser Phe Glu Ile Asn Phe Cys Glu Gly Ser Leu Ser Gly Asn Tyr
            740                 745                 750

Met Lys Ser Met Glu Trp His Ile Gly Cys Lys Pro Gln Glu Val Leu
        755                 760                 765

Gln Cys Ile Gly Gln Leu Ser His Val Thr Thr Leu Lys Ile Val Asn
    770                 775                 780

Ala Leu Asp Leu Leu Thr Cys Arg Val Thr Phe Pro Pro Asn Val Ile
785                 790                 795                 800

Lys Leu Thr Leu Thr Gly Ile Ser Cys Val Thr Asp Glu Gly Met Asp
                805                 810                 815

Ser Leu Gly Asn His Thr Lys Leu Gln Lys Leu Arg Leu Thr Arg Gly
            820                 825                 830

Ile Leu Ser Glu Ser Phe Asp Leu Asn Cys Val Ala Gly Arg Phe Pro
        835                 840                 845

Gln Leu Gln Val Phe Glu Met Ser Gly Leu Lys Val Arg Asn Trp Lys
    850                 855                 860

Leu Gly Asn Ser Ala Met Leu Cys Leu Gln Ser Leu Ile Ile His Lys
865                 870                 875                 880

Cys Lys Met Leu Asp Gly Ile Pro Asn Glu Leu Trp Ser Leu Ile Ala
                885                 890                 895

Leu Arg Lys Val Gln Val Lys Gln Pro Ser Glu Ala Met Ala Arg Met
            900                 905                 910

Leu Gln Asn Leu Glu Met Lys Asp Gly Val Glu Leu Ile Val Glu Pro
        915                 920                 925

Lys Glu Arg His Asp Ser Thr Val Ile Leu Ser Met Asp Glu Ile Trp
    930                 935                 940

Glu Ala Phe Asn Ser Arg Gly Ile Cys
945                 950

<210> SEQ ID NO 5
<211> LENGTH: 2793
<212> TYPE: DNA
<213> ORGANISM: Glycine max

```
<400> SEQUENCE: 5
atggcggaca gtgtggtttc ctttgtatta gatcacttgt ctcaactgat ggcacgtgaa      60
gcaaagttgc tgtgtggcgt ggaagacagg atcaagtccc tccaaaatga gcttgaaatg     120
atcaatgagt tcctcaatac ctcaaagagc aaaaagggga ttgagaaaaa agtggtgagc     180
caaatcagag atgttgccca tctagctgag gatgtcatcg acacatacgt tgccaaagtt     240
gccatacacg agaggagaac catgatgggt aggctcctcc atagcgttca ccaagcaagg     300
ttgctccatg acgtagctga gaaaatagac cagataaaaa acactatcag tgagatacgc     360
aacaacaaga tcaaatatga agaattccaa gaaagcaaca gtcaatccac aacgaaagca     420
gaggaggagg agaaggagaa ggaaagggcg caattactac acaagctaag aagaaatgtg     480
gaggaagaag atgtagtagg ctttgtacgt gactccaacg tagtcatcag gcgactccta     540
gaaggtggtt catctcgtaa cgttgtctcc atcattggca tgggtggatt gggcaagacc     600
acccttgccc gaaaggtcta taacagcaga gaggtgaaac aatactttag atgttgcgcg     660
tgggtttatg tgtcggacga gtgtagagtc aaggagattt ccttggcct tcttaagcat      720 ttgatgccaa accttgaata ccaacgtaga ggcaacacga aggtaagaa acgcacaaga     780 gaatttaaca tttctaagtt gagcgaggag gagttgaaaa aactggtgag agaatgcttg     840
gagaggaaaa ggtatctggt ggtcctcgat gacctgtgga aaacacaaga ttgggacgag     900
ttgcacgatg cttttcctga cgacaacaaa ggcagcagga tattgattac tagtcgtttg     960
aaagaggtgg cgttgcatac tagccatcat cctccttact atcttcagtt tcttagtgaa    1020
gatgaaagtt gggagctctt ctgcaagaaa gtgtttaggg gcgaagagta ctcttctgat    1080
ttggagcctt tggggaaaca gatagttcaa agttgtcgtg gtttgccact ctcaatcgtg    1140
gtgttagcag ggttgctagc caacaaggaa aaatcatata gagaatggtc taaagtggtg    1200
ggtcatgtca actggtatct tactcaagat gagacccaag tgaaggatat agttctcaaa    1260
ctcagctatg acaacctgcc aaggagattg aaaccgtgct ttctgttttct tgggatattc    1320 cccgaagact ttgaaatccc agttaggcca ttattgcaac gatgggttgc cgaaggattt    1380
atacaagaaa cagggaatag agacccagat gatgttgttg aagactactt gtacgagctc    1440
attgatcgta gtttggtcca agtagcagca atgaagacaa gtggaggcgt gaagacttgt    1500
cacatccatg atcttcttcg agatctttgc atatcagaga gcaaagaaga caaggttttc    1560
caagtttgca caggtaataa cattctaatc tccacaaaac cccgcagact gtccattcat    1620
tgtaacatgg gtgactacat ttcttcaaac aacaatgacc agtcatgtat ccgttctttg    1680
ttcatgtttg ggccacgtta tttttttatt ccaagcgagt tgaaaagact tttcaaaggc    1740
ttcaaattgg ttcgagtgtt agagcttgga acagacagtt gtggaggaaa gattccatct    1800
aatttggggg actttatcca cttaaggtat ttgagaattg actcgcaaca tgttagaatt    1860
attccagctt ctatacttac ccttcagaat ttacaaaccg tagacctagg ttgctggcgt    1920
ttgactattc caatttcttt ccctgctcaa atatggaagc tcaaacattt aaggcatttg    1980
tatgctccag ggcctatcaa gcttagaggc cactattcaa aaccaagtga ggttatgtgg    2040
aatcttcaaa ccatgaacgc cattgtgttg gacgaacaag catcatattt gatatataaa    2100
ggaactttcc ccaaccttaa gaatttaggt ctgaaaatat cttcgggtcg caaggctaaa    2160
tggcctaagt tgttgcagag cctactacaa ttaagtcatt tgagtaagtt aaggatttcc    2220
tttgaaatga agttgtttga aggttcagtg tccggaaact atgtgaacag catggagtgg    2280
cacattggtt gtaagccaca agaagtatta caaagcatag ggcagttgag tcatgtaact    2340
```

```
acgctgaata ttcgcaatgc cttggacctt ctaacatgta gggtcacgtt tcctccaaat    2400
gttataaagt taagattgac aggtattagt tgtgtgactg atgagggaat ggattctttg    2460
ggaaatcaca ccaaactcca aaaattgaga ctaacaggag gaattttgtc agaatccttt    2520
gacctcaatt gtgttgcagg aaggttccca caactgcagg tgtttgagat gagtggtttg    2580
aaagttagaa actggaaatt aggcaacagt gcaatgttat gcctccaaag tctgatcatc    2640
caccaatgta aaatgttaga tggcatccca aatgaactgt ggtctttgat tgctttgaga    2700
aaagtgcaag taaagcaacc ctcagaagca atggctcaca tgctacaaaa cttggaaatg    2760
aaggatgggg ttgaacttat agttgaaccg tag                                2793

<210> SEQ ID NO 6
<211> LENGTH: 930
<212> TYPE: PRT
<213> ORGANISM: Glycine max

<400> SEQUENCE: 6
```

Met Ala Asp Ser Val Ser Phe Val Leu Asp His Leu Ser Gln Leu
1               5                   10                  15

Met Ala Arg Glu Ala Lys Leu Leu Cys Gly Val Glu Asp Arg Ile Lys
            20                  25                  30

Ser Leu Gln Asn Glu Leu Glu Met Ile Asn Glu Phe Leu Asn Thr Ser
        35                  40                  45

Lys Ser Lys Lys Gly Ile Glu Lys Lys Val Val Ser Gln Ile Arg Asp
    50                  55                  60

Val Ala His Leu Ala Glu Asp Val Ile Asp Thr Tyr Val Ala Lys Val
65                  70                  75                  80

Ala Ile His Glu Arg Arg Thr Met Met Gly Arg Leu Leu His Ser Val
                85                  90                  95

His Gln Ala Arg Leu Leu His Asp Val Ala Glu Lys Ile Asp Gln Ile
            100                 105                 110

Lys Asn Thr Ile Ser Glu Ile Arg Asn Asn Lys Ile Lys Tyr Glu Glu
        115                 120                 125

Phe Gln Glu Ser Asn Ser Gln Ser Thr Thr Lys Ala Glu Glu Glu Glu
    130                 135                 140

Lys Glu Lys Glu Arg Ala Gln Leu Leu His Lys Leu Arg Arg Asn Val
145                 150                 155                 160

Glu Glu Glu Asp Val Val Gly Phe Val Arg Asp Ser Asn Val Val Ile
                165                 170                 175

Arg Arg Leu Leu Glu Gly Gly Ser Arg Asn Val Val Ser Ile Ile
            180                 185                 190

Gly Met Gly Gly Leu Gly Lys Thr Thr Leu Ala Arg Lys Val Tyr Asn
        195                 200                 205

Ser Arg Glu Val Lys Gln Tyr Phe Arg Cys Cys Ala Trp Val Tyr Val
    210                 215                 220

Ser Asp Glu Cys Arg Val Lys Glu Ile Phe Leu Gly Leu Leu Lys His
225                 230                 235                 240

Leu Met Pro Asn Leu Glu Tyr Gln Arg Arg Gly Asn Thr Lys Gly Lys
                245                 250                 255

Lys Arg Thr Arg Glu Phe Asn Ile Ser Lys Leu Ser Glu Glu Glu Leu
            260                 265                 270

Lys Lys Leu Val Arg Glu Cys Leu Glu Arg Lys Arg Tyr Leu Val Val
        275                 280                 285

-continued

Leu Asp Asp Leu Trp Lys Thr Gln Asp Trp Asp Glu Leu His Asp Ala
290                 295                 300

Phe Pro Asp Asp Asn Lys Gly Ser Arg Ile Leu Ile Thr Ser Arg Leu
305                 310                 315                 320

Lys Glu Val Ala Leu His Thr Ser His His Pro Pro Tyr Tyr Leu Gln
                325                 330                 335

Phe Leu Ser Glu Asp Glu Ser Trp Glu Leu Phe Cys Lys Lys Val Phe
            340                 345                 350

Arg Gly Glu Glu Tyr Ser Ser Asp Leu Glu Pro Leu Gly Lys Gln Ile
        355                 360                 365

Val Gln Ser Cys Arg Gly Leu Pro Leu Ser Ile Val Val Leu Ala Gly
370                 375                 380

Leu Leu Ala Asn Lys Glu Lys Ser Tyr Arg Glu Trp Ser Lys Val Val
385                 390                 395                 400

Gly His Val Asn Trp Tyr Leu Thr Gln Asp Glu Thr Gln Val Lys Asp
                405                 410                 415

Ile Val Leu Lys Leu Ser Tyr Asp Asn Leu Pro Arg Arg Leu Lys Pro
            420                 425                 430

Cys Phe Leu Phe Leu Gly Ile Phe Pro Glu Asp Phe Glu Ile Pro Val
        435                 440                 445

Arg Pro Leu Leu Gln Arg Trp Val Ala Glu Gly Phe Ile Gln Glu Thr
450                 455                 460

Gly Asn Arg Asp Pro Asp Asp Val Val Glu Asp Tyr Leu Tyr Glu Leu
465                 470                 475                 480

Ile Asp Arg Ser Leu Val Gln Val Ala Ala Met Lys Thr Ser Gly Gly
                485                 490                 495

Val Lys Thr Cys His Ile His Asp Leu Leu Arg Asp Leu Cys Ile Ser
            500                 505                 510

Glu Ser Lys Glu Asp Lys Val Phe Gln Val Cys Thr Gly Asn Asn Ile
        515                 520                 525

Leu Ile Ser Thr Lys Pro Arg Arg Leu Ser Ile His Cys Asn Met Gly
530                 535                 540

Asp Tyr Ile Ser Ser Asn Asn Asn Asp Gln Ser Cys Ile Arg Ser Leu
545                 550                 555                 560

Phe Met Phe Gly Pro Arg Tyr Phe Ile Pro Ser Glu Leu Lys Arg
                565                 570                 575

Leu Phe Lys Gly Phe Lys Leu Val Arg Val Leu Glu Leu Gly Thr Asp
            580                 585                 590

Ser Cys Gly Gly Lys Ile Pro Ser Asn Leu Gly Asp Phe Ile His Leu
        595                 600                 605

Arg Tyr Leu Arg Ile Asp Ser Gln His Val Arg Ile Ile Pro Ala Ser
610                 615                 620

Ile Leu Thr Leu Gln Asn Leu Gln Thr Val Asp Leu Gly Cys Trp Arg
625                 630                 635                 640

Leu Thr Ile Pro Ile Ser Phe Pro Ala Gln Ile Trp Lys Leu Lys His
                645                 650                 655

Leu Arg His Leu Tyr Ala Pro Gly Pro Ile Lys Leu Arg Gly His Tyr
            660                 665                 670

Ser Lys Pro Ser Glu Val Met Trp Asn Leu Gln Thr Met Asn Ala Ile
        675                 680                 685

Val Leu Asp Glu Gln Ala Ser Tyr Leu Ile Tyr Lys Gly Thr Phe Pro
690                 695                 700

Asn Leu Lys Asn Leu Gly Leu Lys Ile Ser Ser Gly Arg Lys Ala Lys

```
                        705                 710                 715                 720
Trp Pro Lys Leu Leu Gln Ser Leu Leu Gln Leu Ser His Leu Ser Lys
                725                 730                 735
Leu Arg Ile Ser Phe Glu Met Lys Leu Phe Glu Gly Ser Val Ser Gly
            740                 745                 750
Asn Tyr Val Asn Ser Met Glu Trp His Ile Gly Cys Lys Pro Gln Glu
        755                 760                 765
Val Leu Gln Ser Ile Gly Gln Leu Ser His Val Thr Thr Leu Asn Ile
    770                 775                 780
Arg Asn Ala Leu Asp Leu Leu Thr Cys Arg Val Thr Phe Pro Pro Asn
785                 790                 795                 800
Val Ile Lys Leu Arg Leu Thr Gly Ile Ser Cys Val Thr Asp Glu Gly
                805                 810                 815
Met Asp Ser Leu Gly Asn His Thr Lys Leu Gln Lys Leu Arg Leu Thr
            820                 825                 830
Gly Gly Ile Leu Ser Glu Ser Phe Asp Leu Asn Cys Val Ala Gly Arg
        835                 840                 845
Phe Pro Gln Leu Gln Val Phe Glu Met Ser Gly Leu Lys Val Arg Asn
    850                 855                 860
Trp Lys Leu Gly Asn Ser Ala Met Leu Cys Leu Gln Ser Leu Ile Ile
865                 870                 875                 880
His Gln Cys Lys Met Leu Asp Gly Ile Pro Asn Glu Leu Trp Ser Leu
                885                 890                 895
Ile Ala Leu Arg Lys Val Gln Val Lys Gln Pro Ser Glu Ala Met Ala
            900                 905                 910
His Met Leu Gln Asn Leu Glu Met Lys Asp Gly Val Glu Leu Ile Val
        915                 920                 925
Glu Pro
    930

<210> SEQ ID NO 7
<211> LENGTH: 2847
<212> TYPE: DNA
<213> ORGANISM: Glycine max

<400> SEQUENCE: 7
atggcggaca gtgtggtttc ctttgtatta gatcacttgt ctcaactggt ggcacgtgaa      60
gcaaagttgc tgtgtggcgt ggaagacagg atcaagtccc tccaaaatga gcttgaaatg     120
atcaatgagt tcctcaatac ctcaaagagc aaaaagggga ttgagaaaaa agtggtgagc     180
caaatcagag atgttgccca tctagctgag gatgtcatcg acacatacgt tgccaaagtt     240
gccatacacg agaggaggac catgatgggt aggctcctcc atagcgttca ccaagcaagg     300
ttgctccatg atgtagctga gaaaatagac cagataaaaa acacaatcag tgagatacgc     360
aacaacaaga tcaaatatga agaattccaa gaaagcaaca gtcaatccac aacaaaagca     420
gaggaggagg aagaggagaa ggaaagggcg caattactac acaagctaag aagaaatgtg     480
gaggaagaag atgtagtagg ctttgtacgt gactccaacg tagtcatcaa gcgactccta     540
gacggtggtt catctcgtaa cgttgtctcc atcattggca tggtggatt gggcaagacc     600 acccttgccc gaaaggtcta taacagcaga gaggtgaaac aatacttcag aagttgcgcg     660
tgggtttatg tgtcaaacga gtgtagagtc aaagagattt ccttggcct tcttaagcat     720 ttgatgccaa accttgaata ccaacgtaga ggcaacaaga aaggtaagaa acgcacaaga     780
gaatttaaca tttctaagtt gagcgaggag gagttgaaga aactggtgag agaatgcttg     840
```

```
gagaggaaaa ggtatctggt ggtcctcgat gacctgtgga aaacacaaga ttgggacgag    900
ttgcacgatg cctttcctga cgacaacaaa ggcagcagaa tattgattac tagtcgtttg    960
aaagaggtgg cgttgcatac tagccatcat cctccttact atcttcagtt tcttagtgaa   1020
gatgaaagtt gggagctctt ctgcaagaaa gtgtttaggg gcgaagagta ctcttctgat   1080
ttggagcctt tggggaaaca gatagttcaa agttgtcgtg gtttgccact ctcaatcgtg   1140
gtgttagcag ggttgctagc caacaaggaa aaatcatata gagaatggtc taaagtggtg   1200
ggtcatgtca actggtatct tactcaagat gagacccaag tgaaggatat agttctcaaa   1260
ctcagctatg caacctgcc aaggagattg aaaccgtgct ttctgtttct gggatattc     1320 cccgaagact ttgaaatccc agttaggcca ttattgcaac gatgggttgc cgaaggattt   1380
atacaagaaa cagggaatag agacccagat gatgttgctg aagactactt gtacgagctc   1440
attgatcgta gtttggtcca agtagcagca atgaagacaa gtggaggcgt gaagacttgt   1500
cacatccatg atcttcttcg agatctttgc atatcagaga gcaaagagga caaggttttc   1560
gaagtttgca caggtaataa cattctaatg tccacaaaac cccgcagatt gtccattcat   1620
tgtaacatgg gtgactacat ttcttcaaat aacaatgacc agtcatgtat tcgttctttg   1680
ttcatgtttg ggccacatta tttttttcatc ccaagcgagt tgaaaagact tttcaaaggc   1740
ttcaaattgg ttcgagtgtt agagcttgga acagacagct gcggaggaaa gattccatct   1800
aatttggggg actttatcca cttaaggtat ttgagaattg tctcgaaata tgttagaatt   1860
attcctgctt ctatacttac ccttcagaat ttacaaaccg tagacctagg ttgttggcgt   1920
tgggctactc caatttcttt ccctgtttca atttcttttcc cggctcaaat atggaagctc   1980
aaacatttaa ggcatttgta tgcgccaggg cctatcaagc ttagaggcca ctattcaaaa   2040
ccaagtgagg ttatgtggaa tcttcaaacc atgaatgcca ttgtgttgga cgaacaaaca   2100
tcatatttga taaataaagg aactttcccc aaccttaagg atttaggtct gcaaatatct   2160
tcgggtcgca aggctaaatg gcctaagttg ttgcagagcc tacaacaatt aaatcatttg   2220
agtaagttaa ggatttttctt tgaaatgaag tttcctgaag gttcagtgtc cgaaaactat   2280
gtgaacagca tggagtggca cattggttgt aagccacaag aagtattaca atgcataggg   2340
cagttgagtc atgtaactac gctgaaaatt gtcaatgcct ggaccttct aacatgtagg    2400 gtcacgtttc ctccaaatgt tataaagtta acatttacag gtattagtta tgtgactgat   2460
gagggaatgg attctttggg aaatcacacc aaactccaaa aattgagact aaccggagga   2520
atttggtcag attcctttga cctcaattgt gttgcaggag ggttcccaaa actgcaggtg   2580
tttgagatga gtcgtttgaa cgttagaaac tggaaattag caatagtgc aatgttatgc     2640 ctccaaagtc tgatcatcca caaatgtaaa gtgttagatg gcatcccaaa tgaactgtgg   2700
tctttgattg ccttgagaaa agtgcaagta aagcaaccct cagaagcaat ggctcacatg   2760
ctacaaaact ggaaatgaa ggatgggggtt gaacttatag ttgaaccgga ggaacgtcat    2820
gattctactg tgattatcta tggatga                                        2847
```

<210> SEQ ID NO 8
<211> LENGTH: 948
<212> TYPE: PRT
<213> ORGANISM: Glycine max

<400> SEQUENCE: 8

Met Ala Asp Ser Val Val Ser Phe Val Leu Asp His Leu Ser Gln Leu
1               5                   10                  15

```
Val Ala Arg Glu Ala Lys Leu Leu Cys Gly Val Glu Asp Arg Ile Lys
             20                  25                  30

Ser Leu Gln Asn Glu Leu Glu Met Ile Asn Glu Phe Leu Asn Thr Ser
         35                  40                  45

Lys Ser Lys Lys Gly Ile Glu Lys Lys Val Val Ser Gln Ile Arg Asp
     50                  55                  60

Val Ala His Leu Ala Glu Asp Val Ile Asp Thr Tyr Val Ala Lys Val
 65                  70                  75                  80

Ala Ile His Glu Arg Arg Thr Met Met Gly Arg Leu Leu His Ser Val
                 85                  90                  95

His Gln Ala Arg Leu Leu His Asp Val Ala Glu Lys Ile Asp Gln Ile
            100                 105                 110

Lys Asn Thr Ile Ser Glu Ile Arg Asn Asn Lys Ile Lys Tyr Glu Glu
        115                 120                 125

Phe Gln Glu Ser Asn Ser Gln Ser Thr Thr Lys Ala Glu Glu Glu Glu
    130                 135                 140

Glu Lys Glu Arg Ala Gln Leu Leu His Lys Leu Arg Arg Asn Val
145                 150                 155                 160

Glu Glu Glu Asp Val Val Gly Phe Val Arg Asp Ser Asn Val Val Ile
                165                 170                 175

Lys Arg Leu Leu Asp Gly Gly Ser Ser Arg Asn Val Val Ser Ile Ile
            180                 185                 190

Gly Met Gly Gly Leu Gly Lys Thr Thr Leu Ala Arg Lys Val Tyr Asn
        195                 200                 205

Ser Arg Glu Val Lys Gln Tyr Phe Arg Ser Cys Ala Trp Val Tyr Val
    210                 215                 220

Ser Asn Glu Cys Arg Val Lys Glu Ile Phe Leu Gly Leu Leu Lys His
225                 230                 235                 240

Leu Met Pro Asn Leu Glu Tyr Gln Arg Gly Asn Lys Lys Gly Lys
                245                 250                 255

Lys Arg Thr Arg Glu Phe Asn Ile Ser Lys Leu Ser Glu Glu Glu Leu
            260                 265                 270

Lys Lys Leu Val Arg Glu Cys Leu Glu Arg Lys Arg Tyr Leu Val Val
        275                 280                 285

Leu Asp Asp Leu Trp Lys Thr Gln Asp Trp Asp Glu Leu His Asp Ala
    290                 295                 300

Phe Pro Asp Asp Asn Lys Gly Ser Arg Ile Leu Ile Thr Ser Arg Leu
305                 310                 315                 320

Lys Glu Val Ala Leu His Thr Ser His His Pro Pro Tyr Tyr Leu Gln
                325                 330                 335

Phe Leu Ser Glu Asp Glu Ser Trp Glu Leu Phe Cys Lys Lys Val Phe
            340                 345                 350

Arg Gly Glu Glu Tyr Ser Ser Asp Leu Glu Pro Leu Gly Lys Gln Ile
        355                 360                 365

Val Gln Ser Cys Arg Gly Leu Pro Leu Ser Ile Val Val Leu Ala Gly
    370                 375                 380

Leu Leu Ala Asn Lys Glu Lys Ser Tyr Arg Glu Trp Ser Lys Val Val
385                 390                 395                 400

Gly His Val Asn Trp Tyr Leu Thr Gln Asp Glu Thr Gln Val Lys Asp
                405                 410                 415

Ile Val Leu Lys Leu Ser Tyr Asp Asn Leu Pro Arg Arg Leu Lys Pro
            420                 425                 430
```

```
Cys Phe Leu Phe Leu Gly Ile Phe Pro Glu Asp Phe Glu Ile Pro Val
            435                 440                 445

Arg Pro Leu Leu Gln Arg Trp Val Ala Glu Gly Phe Ile Gln Glu Thr
450                 455                 460

Gly Asn Arg Asp Pro Asp Val Ala Glu Asp Tyr Leu Tyr Glu Leu
465                 470                 475                 480

Ile Asp Arg Ser Leu Val Gln Val Ala Ala Met Lys Thr Ser Gly Gly
                485                 490                 495

Val Lys Thr Cys His Ile His Asp Leu Leu Arg Asp Leu Cys Ile Ser
            500                 505                 510

Glu Ser Lys Glu Asp Lys Val Phe Glu Val Cys Thr Gly Asn Asn Ile
            515                 520                 525

Leu Met Ser Thr Lys Pro Arg Arg Leu Ser Ile His Cys Asn Met Gly
530                 535                 540

Asp Tyr Ile Ser Ser Asn Asn Asp Gln Ser Cys Ile Arg Ser Leu
545                 550                 555                 560

Phe Met Phe Gly Pro His Tyr Phe Phe Ile Pro Ser Glu Leu Lys Arg
                565                 570                 575

Leu Phe Lys Gly Phe Lys Leu Val Arg Val Leu Glu Leu Gly Thr Asp
            580                 585                 590

Ser Cys Gly Gly Lys Ile Pro Ser Asn Leu Gly Asp Phe Ile His Leu
            595                 600                 605

Arg Tyr Leu Arg Ile Val Ser Lys Tyr Val Arg Ile Ile Pro Ala Ser
            610                 615                 620

Ile Leu Thr Leu Gln Asn Leu Gln Thr Val Asp Leu Gly Cys Trp Arg
625                 630                 635                 640

Trp Ala Thr Pro Ile Ser Phe Pro Val Ser Ile Ser Phe Pro Ala Gln
                645                 650                 655

Ile Trp Lys Leu Lys His Leu Arg His Leu Tyr Ala Pro Gly Pro Ile
            660                 665                 670

Lys Leu Arg Gly His Tyr Ser Lys Pro Ser Glu Val Met Trp Asn Leu
            675                 680                 685

Gln Thr Met Asn Ala Ile Val Leu Asp Glu Gln Thr Ser Tyr Leu Ile
690                 695                 700

Asn Lys Gly Thr Phe Pro Asn Leu Lys Asp Leu Gly Leu Gln Ile Ser
705                 710                 715                 720

Ser Gly Arg Lys Ala Lys Trp Pro Lys Leu Leu Gln Ser Leu Gln Gln
                725                 730                 735

Leu Asn His Leu Ser Lys Leu Arg Ile Phe Phe Glu Met Lys Phe Pro
            740                 745                 750

Glu Gly Ser Val Ser Glu Asn Tyr Val Asn Ser Met Glu Trp His Ile
            755                 760                 765

Gly Cys Lys Pro Gln Glu Val Leu Gln Cys Ile Gly Gln Leu Ser His
            770                 775                 780

Val Thr Thr Leu Lys Ile Val Asn Ala Leu Asp Leu Leu Thr Cys Arg
785                 790                 795                 800

Val Thr Phe Pro Pro Asn Val Ile Lys Leu Thr Phe Thr Gly Ile Ser
                805                 810                 815

Tyr Val Thr Asp Glu Gly Met Asp Ser Leu Gly Asn His Thr Lys Leu
            820                 825                 830

Gln Lys Leu Arg Leu Thr Gly Gly Ile Trp Ser Asp Ser Phe Asp Leu
            835                 840                 845

Asn Cys Val Ala Gly Arg Phe Pro Lys Leu Gln Val Phe Glu Met Ser
```

-continued

```
                850                 855                 860
Arg Leu Asn Val Arg Asn Trp Lys Leu Gly Asn Ser Ala Met Leu Cys
865                 870                 875                 880

Leu Gln Ser Leu Ile Ile His Lys Cys Lys Val Leu Asp Gly Ile Pro
                885                 890                 895

Asn Glu Leu Trp Ser Leu Ile Ala Leu Arg Lys Val Gln Val Lys Gln
                900                 905                 910

Pro Ser Glu Ala Met Ala His Met Leu Gln Asn Leu Glu Met Lys Asp
            915                 920                 925

Gly Val Glu Leu Ile Val Glu Pro Glu Glu Arg His Asp Ser Thr Val
        930                 935                 940

Ile Ile Tyr Gly
945
```